United States Patent [19]
Hakomori et al.

[11] Patent Number: 5,171,667
[45] Date of Patent: Dec. 15, 1992

[54] HYBRIDOMAS PRODUCING MONOCLONAL ANTIBODIES TO MONO-, DI- AND TRIFUCOSYLATED TYPE 2 CHAIN

[75] Inventors: Sen-itroh Hakomori, Mercer Island, Wash.; Yasuo Fukushi, Sendai, Japan

[73] Assignee: Fred Hutchinson Cancer Research Center, Seattle, Wash.

[21] Appl. No.: 385,303

[22] Filed: Jul. 25, 1989

Related U.S. Application Data

[62] Division of Ser. No. 728,821, Apr. 4, 1985, Pat. No. 4,876,199.

[51] Int. Cl.$^5$ .................. C12P 21/08; C07K 15/28; A61K 43/00; C12N 5/20
[52] U.S. Cl. .................. 435/7.23; 530/391.3; 530/387.5; 530/388.1; 530/388.8; 424/1.1; 424/9; 424/85.8; 424/85.91; 435/172.2; 435/70.21; 435/240.27; 935/92; 935/104; 935/107
[58] Field of Search ............ 424/1.1, 9, 85.8, 85.91; 435/172.2, 70.21, 240.27, 948, 7.23; 935/92, 104, 107; 530/387, 391, 391.3, 387.5, 388, 388.8

[56] References Cited

U.S. PATENT DOCUMENTS 4,678,747  7/1987  Lloyd et al. .................. 435/7.23
4,876,199 10/1989  Hakomori et al. ............ 435/240.27

OTHER PUBLICATIONS

Fukushi, Y. et al. "Novel Fucolipids accumulating in human adenocarcinoma, II, Selective isolation of hybridoma antibodies that differentially recognize mono-, d-, and trifucosylated type 2 chain", J. Biol. Chem. 259(7):4681–4685, Apr. 10, 1984.

Kannagi, R. et al. "A series of human erythrocyte glycosphinolipids reacting to the monoclonal antibody directed to a developmentally regulated antigen, SSEA-1," J. Biol Chem. 257(24):14865–14874, 1982.

Itzkowitz, S. H., et al., Lewis$^x$-and sialylated Lewis$^x$-related antigen expression in human malignant and nonmalignant colonic tissues, Cancer Res. 46:2627–2632, 1986.

Fukushi, Y., et al., Changes of Le$^x$ and dimeric Le$^x$ haptens and their sialylated antigens during development of human kidney and kidney tumors, J. Urol. 135:1048–1056, 1986.

Yuan, M., et al., Expression of Lewis$^x$ and sialylated Lewis$^x$ antigens in human colorectal polyps, JNCI 78(3):479–488, 1987.

Kim, Y. S., et al., Le$^x$ and Le$^y$ antigen expression in human pancreatic cancer, Cancer Res. 48:475–482, 1988.

Ochi, T., et al., The presence of a myeloid cell population showing strong reactivity with monoclonal antibody directed to difucosyl type 2 chain in epiphyseal bone marrow adjacent to joints affected with rheumatoid arthritis (RA) and its absence in the corresponding normal and non-RA bone marrow, J. Rheumatol. 15(11):1609–1615, 1988.

Nakasaki, H., et al., Mosaicism in the expression of tumor-associated carbohydrate antigens in human colonic and gastric cancers, Cancer Res. 49:3662–3669, Jul. 1, 1989.

Anonymous, Center research targets tumors with radiation, Quest 4(2), pp. 1, 4, and 6, Apr. 1990.

*Primary Examiner*—John J. Doll
*Assistant Examiner*—Paula Hutzell
*Attorney, Agent, or Firm*—Christensen, O'Connor, Johnson & Kindness

[57] ABSTRACT

Hybridoma cell lines that produce monoclonal antibodies that differentially recognize glycolipids with mono-, di-, and trifucosylated type 2 chain structures are disclosed. The monoclonal antibodies can be used to detect specific types of tumor cells that are characterized by enrichment in mono-, di-, or trifucosylated type 2 chain structure. As such, the antibodies produced by the hybridoma cell lines are useful for diagnosis and treatment of human cancer. Also disclosed is an improved method of raising hybridoma cell lines by selecting the hybridomas by positive reactively with one or more fucosylated type 2 chain structures selected from the group consisting of III$^3$FucnLc$_4$, V$^3$FucnLc$_6$, III$^3$-FucnLc$_6$, III$^3$V$^3$Fuc$_2$nLc$_6$, and III$^3$V$^3$VII$^3$Fuc$_3$nLc$_8$.

7 Claims, 16 Drawing Sheets

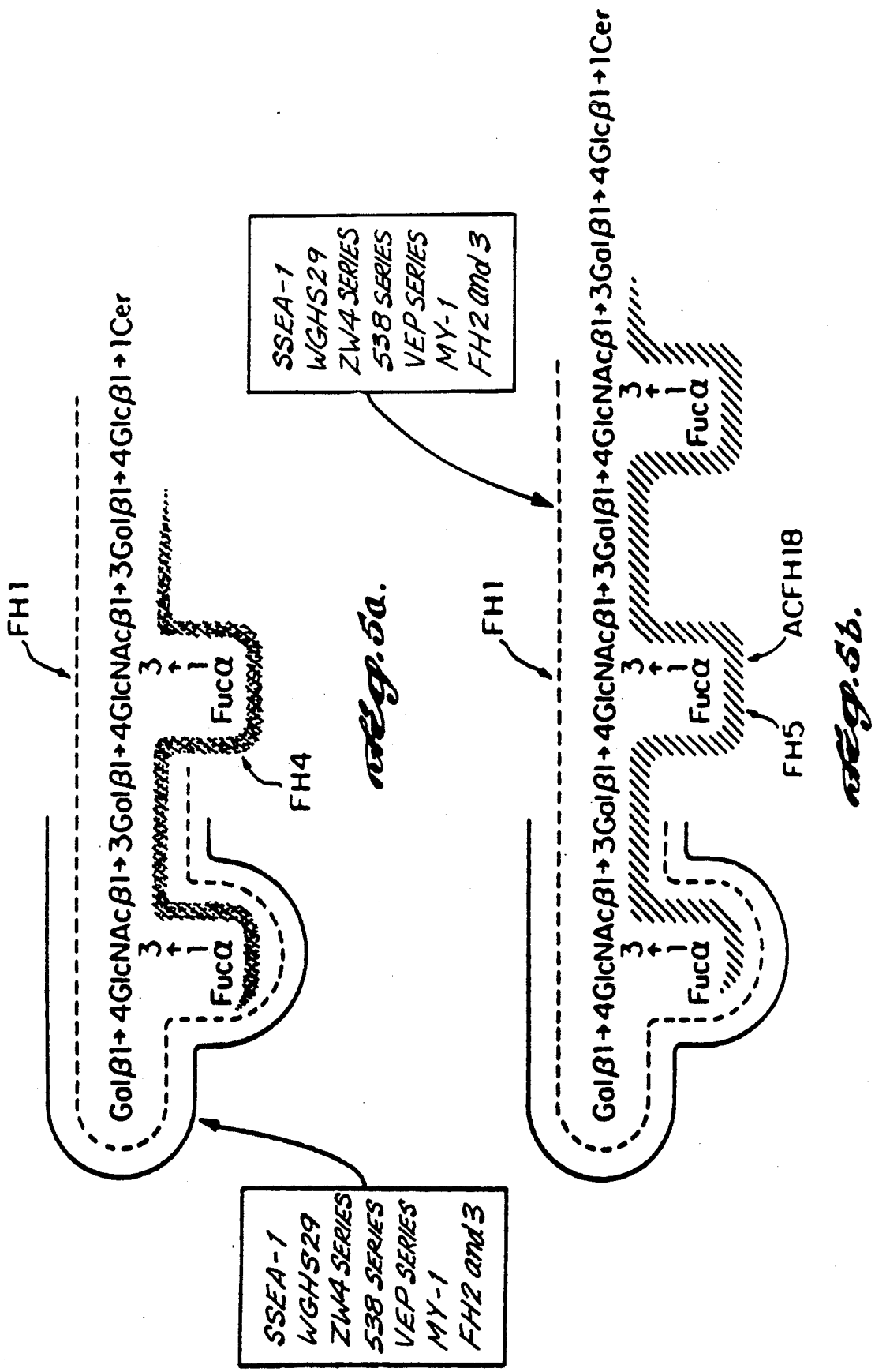

HYBRIDOMAS PRODUCING MONOCLONAL ANTIBODIES TO MONO-, DI- AND TRIFUCOSYLATED TYPE 2 CHAIN

This invention was made partly with Government support under Grants GM23100 and CA20026 from the National Institutes of Health. The Government has certain rights in this invention.

This is a divisional of the prior application Ser. No. 06/728,821, now U.S. Pat. No. 4,876,199, filed Apr. 4, 1985, the benefit of the filing date of which is hereby claimed under 35 U.S.C. § 120.

TECHNICAL FIELD

This invention relates to hybridoma cell lines that produce monoclonal antibodies useful for the detection and treatment of human cancers.

BACKGROUND OF THE INVENTION

Some tumor cells have been characterized by the presence of unique glycolipid markers which are absent or expressed minimally at normal cell surfaces. Accumulation of a series of fucolipids having the X determinant (Gal$\beta$1→4[Fuc$\alpha$1→3]GlcNAc) at the terminus and Fuc$\alpha$1→3 at the internal GlcNAc residue of unbranched type 2 chain (Gal $\beta$1→4[GlcNAc$\beta$1→3Gal]$_n$ $\beta$1→4GlcNAc→R) is one of the most characteristic membrane phenotypes detected in various human adenocarcinomas. III$^3$FucnLc$_4$ (Formula a, Table I) was found to accumulate in some adenocarcinomas. *J. Biol. Chem.* 246: 1192-1200 (1971); *Biochem. Biophys. Res. Commun.* 100: 1578-1586 (1981). Monofucosylated type 2 chain, previously designated as y$_2$ (V$^3$FucnLc$_6$) (Formula b, Table I), z$_1$ (VII$^3$FucnLc$_8$), and z$_2$ (V$^3$VII$^3$Fuc$_2$nLc$_8$) were isolated and characterized as normal cell components. *J. Biol. Chem.* 252: 14865-14874 (1982). Difucosylated lacto-N-norhexaosylceramide (Formula d, Table I) was implicated in adenocarcinoma of liver but absent in normal liver cells. *Biochem. Biophys. Res. Comm.* 109(1): 36-44 (1982). All these cell surface components have the X determinant structure at the terminus and, therefore, have been detected by immunostaining with monoclonal antibodies directed to the X determinant, such as anti-SSEA-1, WGHS 29, ZWG 13, 14, 111, 538 F12, 538 F8, VEP8, VEP9, My-1, etc. None of these previously established monoclonal antibodies, however, can distinguish among various fucosylated type 2 chain structures such as those associated with human adenocarcinoma cells.

SUMMARY OF THE INVENTION

The present invention provides hybridoma cell lines that produce monoclonal antibodies that differentially recognize glycolipids with mono-, di-, and trifucosylated type 2 chain structures. The monoclonal antibodies of this invention can be used to detect specific types of tumor cells that are characterized by enrichment in mono-, di-, or trifucosylated type 2 chain structure. As such, the antibodies produced by the hybridoma cell lines of this invention are useful for diagnosis and treatment of human cancer. The invention also provides an improved method of raising hybridoma cell lines by selecting the hybridomas by positive reactivity with one or more fucosylated type 2 chain structures selected from the group consisting of III$^3$FucnLc$_4$, V$^3$FucnLc$_6$, III$^3$FucnLc$_6$, III$^3$V$^3$Fuc$_2$nLc$_6$, and III$^3$V$^3$VII$^3$Fuc$_3$nLc$_8$.

The antibody FH4 produced by hybridoma cell line ATCC No. HB8775 shows a remarkable preferential reactivity towards di-or trifucosylated type 2 chain, i.e., it does not react with monofucosylated structures, including lactofucopentaosyl (III) ceramide (III$^3$-FucnLc$_4$), monofucosyl neolactonorhexaosylceramide (y$_2$, V$^3$FucnLc$_6$), and monofucosyl neolactonoroctaosylceramide (z$_1$, VII$^3$FucnLc$_8$), but reacts well with di- and trifucosylated type 2 chain structures such as difucosyl neolactonorhexaosylceramide (III$^3$V$^3$Fuc$_2$nLc$_6$) and trifucosyl neolactonoroctaosylceramide (III$^3$V$^3$VII$^3$Fuc$_3$nLc$_8$).

Two other monoclonal antibodies, FH5 produced by hybridoma cell and ACFH18 line ATCC No. HB8770 preferentially react with trifucosylated type 2 chain structure (III$^3$V$^3$VII$^3$Fuc$_3$nLc$_8$), although cross-reactivity with difucosylated type 2 chain (III$^3$V$^3$Fuc$_2$nLc$_6$) was observed. Both FH5 and ACFH18 showed a minimal cross-reaction with monofucosylated type 2 chain.

In contrast, the antibody FH1 does not react with III$^3$FucnLc$_4$ but reacts with V$^3$FucnLc$_6$, III$^3$V$^3$Fuc$_2$nLc$_6$, and III$^3$V$^3$VII$^3$Fuc$_3$nLc$_8$.

Two monoclonal antibodies, FH2 and FH3, do not discriminate among various glycolipids having fucosylated type 2 chain, and their reactivities are essentially similar to previously established antibodies directed to the terminal X determinant, such as anti-SSEA-1, WGHS 29, VEP8 and 9, My-1, etc.

BRIEF DESCRIPTION OF THE DRAWINGS

FIG. 5 is a diagrammatic representation of the epitope structure recognized by the present FH series and ACFH18 monoclonal antibodies and by previously established monoclonal antibodies directed to the X determinant;

FIG. 12 is a paraffin-embedded section of esophagus tissue of 60-d-old embryo stained by FH3, showing positive staining localized in the solid epithelial area (internal lumen of esophagus is not yet opened at this stage) indicated by arrows a;

DETAILED DESCRIPTION OF THE PREFERRED EMBODIMENTS

Figure 1A:
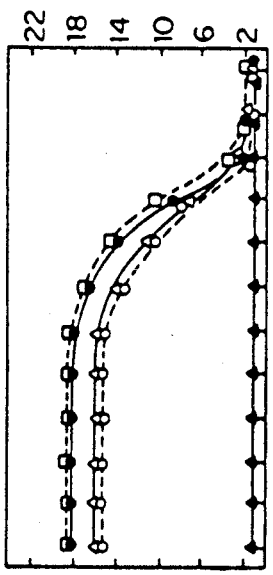
FIG. 1 is a series of graphs that show the reactivity of the monoclonal antibodies FH1, 2, 3, 4, and 5 with various glycolipid antigens at different concentrations of antibodies, wherein graphs A-E show the reactivity of FH1, 2, 3, 4, and 5, respectively, and wherein the various glycolipid antigens are represented as follows: ●, III$^3$V$^3$Fuc$_2$nLc$_6$; △, V$^3$FucnLc$_6$; ○, III$^3$FucnLc$_4$; □, III$^3$V$^3$VII$^3$Fuc$_3$nLc$_8$; ▲, III$^3$FucnLc$_6$.
Figure 1B:
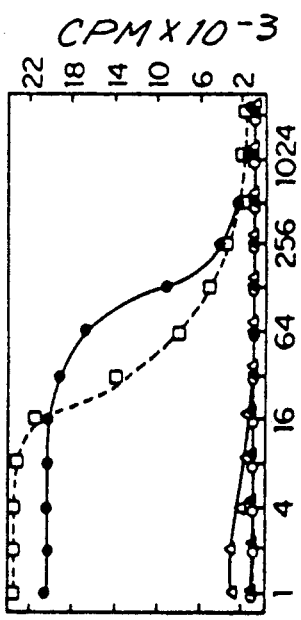

The glycolipid designations used herein, according to the recommendations of the Nomenclature Committee of the International Union of Pure and Applied Chemistry, are as follows: III$^3$FucnLc$_4$, lactofucopentaosyl (III) ceramide; III$^3$V$^3$Fuc$_2$nLc$_6$, difucosyl neolactonorhexaosylceramide; III$^3$V$^3$VII$^3$Fuc$_3$nLc$_8$, trifucosyl neolactonorhexaosylceramide, V$^3$FucnLc$_6$, monofucosyl neolactonorhexaosylceramide, VII$^3$FucnLc$_8$, monofucosyl neolactonoroctaosylceramide; and V$^3$VII$^3$Fuc$_2$nLc$_8$, difucosyl neolactonoroctaosylceramide.

The representative antibodies FH4 and FH5 are produced by hybridoma cell lines ATCC Nos. HB8775 and HB8770, respectively, which were deposited on Apr. 2 and Mar. 26, 1985, at the American Type Culture Collection, 12301 Parklawn Drive, Rockville, MD 20852.

A series of glycolipids having the X determinant (Gal$\beta$1→4[Fuc$\alpha$1→3] GlcNAc) at the terminus and a fucosyl $\alpha$1→3 residue at the internal GlcNAc residue have been isolated and characterized from tumor tissues. Specifically, the glycolipids III$^3$V$^3$Fuc$_2$nLc$_6$ (Formula d, Table I) and III$^3$V$^3$VII$^3$Fuc$_3$nLc$_8$ (Formula e, Table I) have been isolated and chemically characterized as the major components accumulating in human primary liver adenocarcinoma and colonic adenocarcinoma, as described in Hakomori, S., et al., *J. Biol. Chem.* 259: 4672–4680 (1984), hereby incorporated in its entirety by reference. Since accumulation of difucosyl neolactonorhexaosylceramide and trifucosyl neolactonoroctaosylceramide is a characteristic membrane phenotype of various human cancers, it is highly desirable to establish hybridoma antibodies that react specifically to these tumor-associated structures and that do not react to monofucosylated type 2 chain with the X determinant at the terminus.

FIRST SERIES OF EXPERIMENTS

Selective isolation of hybridoma antibodies that differentially recognize mono-, di-, and trifucosylated type 2 chain The general procedure described by Köhler and Milstein for establishing hybridomas producing monoclonal antibodies was followed, and specifically a modification of that procedure was employed as described in *J. Exp. Med.* 150: 1008–1009 (1979). The glycolipids designated III$^3$FucnLc$_4$, III$^3$V$^3$Fuc$_2$nLc$_6$, and III$^3$V$^3$VII$^3$Fuc$_3$nLc$_8$ were prepared from human adenocarcinoma as described in *J. Biol. Chem.* 259: 4672–4680 (1984). The y$_2$(V$^3$FucnLc$_6$) and z$_1$ (VII$^3$FucnLc$_8$) glycolipids were prepared from human adenocarcinoma and human erythrocytes as described in *J. Biol. Chem.* 257: 14865–14874 (1982).

Immunization of Balb/c mice was performed in one series of experiments with a membrane fraction and in another series of experiments with glycolipids adsorbed to *Salmonella minnesota*. The membrane fraction that was used for immunization was prepared by the following procedure. 1.5–2 g of tumor tissue or cells (colonic cancer metastatic to liver tumor cell line TG115 or gastric cancer cell line MKN74) were homogenized in a Dounce homogenizer with 10 ml of distilled water containing 10 kallikrein inhibitor units of "aprotinin" (protease inhibitor; Sigma). After about 50 strokes in an ice-water bath, the homogenate was centrifuged at 2000 rpm for 10 min, and the supernatant was separated and centrifuged at 35,000 rpm for 1 h. The pellet was suspended in 10 ml of distilled water containing aprotinin, and the protein concentration was adjusted to 2.5 mg/ml. An aliquot of 0.5 ml containing 1.25 mg of protein was injected 4 times intraperitoneally on every 4th day. Fusion of the host spleen cells with commercially available mouse myeloma SP/2 cells was performed on the 3rd day after the last injection. In one experiment, only one intravenous injection with the membrane preparation was made, followed by fusion with SP/2 after 3 days. Cloning of hybridomas was performed on plates coated with purified $III^3V^3Fuc_2nLc_6$, $III^3FucnLc_4$, and $V^3FucnLc_6$.

In the other series of experiments, a pure glycolipid was used as immunogen with S. minnesota as the carrier. J. Exp. Med. 150: 1008–1019 (1979); Eur. J. Biochem. 24: 116–122 (1971). An ethanol solution (50 μl) containing 20 μg of a purified glycolipid, $III^3V^3Fuc_2nLc_6$, was mixed with 800 μl of phosphate-buffered saline (pH 7.4). The solution was further mixed with 250 μg of acid-treated S. minnesota suspended in 250 μl of phosphate-buffered saline. The whole mixture was thoroughly mixed at 40° C. The suspension containing 5 μg of glycolipid was intravenously injected on the 1st day; subsequently, an aliquot containing 2 μg of glycolipid was injected 3 times on every 4th day. The fusion of the host spleen cells with mouse myeloma SP/2 cells was performed on the 3rd day after the last injection. The hybridoma was cloned on 96-well plates (Dynatech Immunolon, Dynatech Laboratories, Inc., Alexandria, VA) coated with purified glycolipid (10 ng/well) and cholesterol (30 ng/well) and lecithin (50 ng/well). Cloning was performed repeatedly.

Various type 2 chain glycolipids with X determinant structure were fully characterized by methylation analysis and $^1$H-NMR spectroscopy as described in J. Biol. Chem. 259: 4672–4680 (1984). Hybridomas were selected by positive reactivity with desired glycolipid antigen and negative reactivity with undesired glycolipid antigen as stated in Table I. For example, FH4 was selected by positive reactivity (+) with di- and trifucosyl type 2 chain with X structure ($III^3V^3Fuc_2nLc_6$ and $III^3V^3VII^3Fuc_3nLc_8$) and negative reactivity (−) with various other monofucosyl type 2 chain structures. The reactivity of the antibody was based on solid phase radioimmunoassay, i.e., antibody binding to glycolipids adsorbed on plastic surfaces with cholesterol and lecithin, as described in Cancer Res. 43: 4997–5005 (1983).

Of many hybridomas produced, six clones were established which produce ascites with high antibody titer. The monoclonal antibodies that are capable of distinguishing among various fucosylated type 2 chain glycolipids and their specificities and immunoglobulin class are listed in Table I.

TABLE I
Properties of monoclonal antibodies directed to various fucosylated type 2 chain structures

| Hybridoma | Ig class | Method of preparation | Reactivities with $III^3FucnLc_4$[a] |
|---|---|---|---|
| FH1 | IgM | TG115 membrane; intraperitoneal injection; 4 × selected by glycolpid | − |
| FH2 | IgM | As above | + |
| FH3 | IgG3 | $III^3V^3Fuc_2nLc_6$ and S. minnesota; intravenous injection; 4 × selected by glycolipid | + |
| FH4 | IgG3 | As above | − |
| FH5 | IgM | TG115 membrane; intravenous injection; 1 × selected by glycolipid | − |
| ACFH18 | IgM | MKN74 cell membrane; intraperitoneal injection; 4 × selected by glycolipid | − |

| Hybridoma | Reactivities with | | | | |
|---|---|---|---|---|---|
|  | $V^3FucnLc_6$[b] | $III^3FucnLc_6$[c] | $III^3V^3$-$Fuc_2nLc_6$[d] | $III^3V^3VII^3$-$Fuc_3nLc_8$[e] | $VI^2FucnLc_6$ (H$_2$ glycolipid)[f] |
| FH1 | + | − | + | + | − |
| FH2 | + | − | + | + | − |
| FH3 | + | − | + | + | − |
| FH4 | − | − | ++ | ++ | − |
| FH5 | ± | − | ± | ++ | − |

TABLE I-continued
Properties of monoclonal antibodies directed to various fucosylated type 2 chain structures

| | | | | | |
|---|---|---|---|---|---|
| ACFH18 | ± | − | + | ++ | − |

$^a$Gal$\beta$1→4GlcNA$\beta$1→3Gal$\beta$1→4Glc$\beta$1→1Cer
  3
  ↑
  Fuc$\alpha$1

$^b$Gal$\beta$1→4GlcNAc$\beta$1→3Gal$\beta$1→4GlcNAc$\beta$1→3Gal$\beta$1→4Glc$\beta$1→1Cer
  3
  ↑
  Fuc$\alpha$1

$^c$Gal$\beta$1→4GlcNAc$\beta$1→3Gal$\beta$1→4GlcNAc$\beta$1→3Gal$\beta$1→4Glc$\beta$1→1Cer
                          3
                          ↑
                          Fuc$\alpha$1

$^d$Gal$\beta$1→4GlcNAc$\beta$1→3Gal$\beta$1→4GlcNAc$\beta$1→3Gal$\beta$1→4Glc$\beta$1→1Cer
  3                       3
  ↑                       ↑
  Fuc$\alpha$1             Fuc$\alpha$1

$^e$Gal$\beta$1→4GlcNAc$\beta$1→3Gal$\beta$1→4GlcNAc$\beta$1→3Gal$\beta$1→4GlcNAc$\beta$1→3Gal$\beta$1→4Glc$\beta$1→1Cer
  3                       3                       3
  ↑                       ↑                       ↑
  Fuc$\alpha$1             Fuc$\alpha$1             Fuc$\alpha$1

$^f$Gal$\beta$1→4GlcNAc$\beta$1→3Gal$\beta$1→4GlcNAc$\beta$1→3Gal$\beta$1→4Glc$\beta$1→1Cer
  2
  ↑
  Fuc$\alpha$1

The clones that produce the monoclonal antibodies FH4 and FH5 listed in Table I have been deposited in the American Type Culture Collection, 12301 Parklawn Drive, Rockville, Md., USA 20852. The deposited hybridoma cell lines and the monoclonal antibodies they respectively produce are as follows: ATCC No. HB8775, FH4; ATCC No. HB8770, FH5.

Methods for culturing and harvesting the hybridomas

No special methods are employed for culturing and harvesting antibodies from the above-referenced hybridomas. The hybridoma cell can be grown very well in regular hybridoma medium, e.g., RPMI medium supplemented with 15% fetal calf serum. However, immunization after cells are thawed from stock vial requires special care to start cell proliferation, particularly for hybridoma ATCC No. HB8775 that produces antibody FH4. Procedures for thawing and growing the hybridoma producing FH4 and the other hybridomas are described below. For production of ascites, $5 \times 10^5$ cells can be injected into the peritoneal cavity of Balb/c mice that have been pre-treated with 0.5% Pristane in accordance with standard methodology. Cells can also be grown in chemically-defined medium established for hybridomas such as described in *Anal. Biochem.* 102: 255-270 (1980).

IgG3 antibody either in culture medium or ascites can be directly purified by protein A-Sepharose column, and IgM antibody can be purified by gel filtration on Sepharose 4B column; both in accordance with established methodology.

Procedures for thawing and growing the hybridoma cell line producing antibody FH4.

Each vial typically contains about $5 \times 10^5$ cells. Thaw a vial rapidly at 37° C., then centrifuge at 800 rpm for one minute to separate cells from freezing media. Cells in pellet are suspended in RPMI media supplemented with 15% fetal calf serum, and transferred in 8 ml volume of the same media with fetal calf serum placed in a small flask (25 ml) to which ¼ part of thymocytes derived from a single whole thymus of Balb/c mice are added. Fetal calf serum should be proven to be suitable for growing hybridoma cells. Thymocytes are prepared from a thymus excised from 2-3 week old Balb/c mice (male or female). Hybridoma cells and thymocytes in a 25 ml flask are incubated in a $CO_2$ incubator for one day and 8 ml of new media added, and further incubated for three days. Observe cells are proliferating during this time. The culture is divided into two flasks of the same size, and to each flask 8 ml of new media is added. Cells are thereby passed to a new medium at every three days. Within ten days after cells are thawed, cells growing in one or a few flasks are injected into pristane-primed peritoneal cavity of Balb/c mice.

Procedures for thawing and growing the hybridoma cell lines producing antibodies FH1, 2, 3, 5, or ACFH18

The procedure is the same as above but can be simplified without addition of thymocytes. The culture schedule is the same as above recommendation. Injection of cells into peritoneal cavity to obtain ascites is not necessary within ten days after thawing. Injection can be made at any time.

Reactivities of the antibodies with various types of glycolipids having fucosylated type 2 chain structure The reactivities of the antibodies with various types of glycolipids having fucosylated type 2 chain structure are shown in FIGS. 1 and 2. The reactivity of varying concentrations of the antibodies with constant quantities of glycolipids is shown in FIG. 1, and the reactivity of the antibodies with varying quantities of glycolipid antigens is shown in FIG. 2. Solid phase radioimmunoassay was performed on a detachable vinyl strip (Costar, Cambridge, Ma.) as described in *Cancer Res.* 43: 4997-5005 (1983).

Specifically, FIG. 1 shows the reactivity of the monoclonal antibodies FH1, 2, 3, 4, and 5 with various glycolipid antigens at different concentrations of antibodies. The assay was made on vinyl strips coated with glycolipids, cholesterol, and lecithin. The quantity of glycolipid per well was 10 ng with 30 ng of cholesterol and 50 ng of lecithin. FIG. 2 shows the reactivity of the monoclonal antibodies FH1, 2, 3, 4, 5, and ACFH18 at different concentrations of glycolipid antigens. The initial concentration of glycolipid coated on a vinyl strip was 30 ng with 90 ng of cholesterol and 150 ng of lecithin. The antibody concentration applied to each well was constant at a 1:100 dilution of the culture supernatant.

Figure 2B:
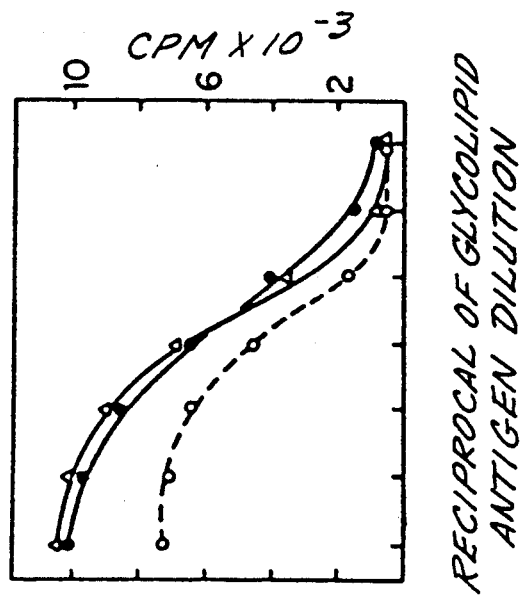
FIG. 2 is a series of graphs that show the reactivity of the monoclonal antibodies FH1, 2, 3, 4, 5, and ACFH18 at different concentrations of glycolipid antigens, wherein graphs A-E show the reactivity of FH 1, 2, 3, 4, and 5, respectively, and F shows the reactivity of ACFH18, and wherein the symbol for each glycolipid is the same as for FIG. 1, except X, for z$_1$ (VII$^3$FucnLc$_8$), is added in F.
Figure 2A:
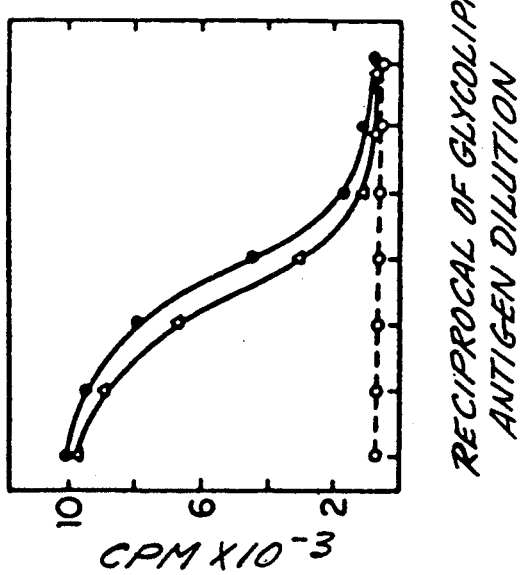

Referring to FIG. 1A and FIG. 2A, the antibody FH1 reacted with tri-, di-, and monofucosylated type 2 chain equally well, although it did not react with $III^3$-FucnLc$_4$.

Referring to FIGS. 1, B and C, and FIGS. 2, B and C, the antibodies FH2 and FH3, in contrast to FH1, reacted with all fucosylated type 2 chain glycolipids, including lactofucopentaosyl(III)ceramide, although a subtle difference in the order of reactivity was observed between FH2 and FH3.

Figure 1E:
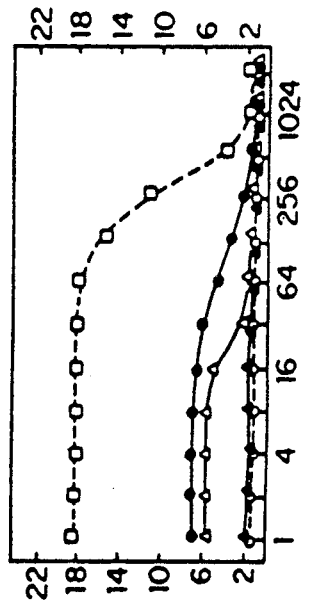
Figure 1C:
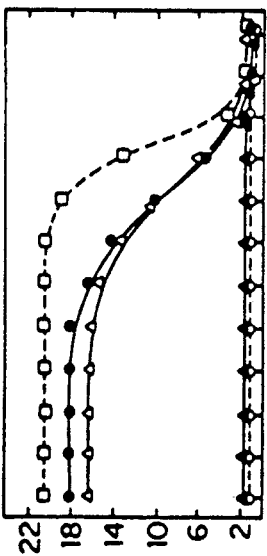
Figure 1D:
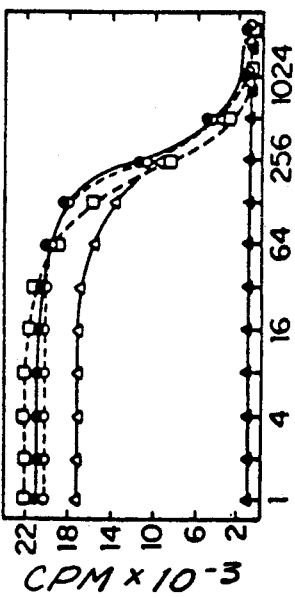
Figure 2D:
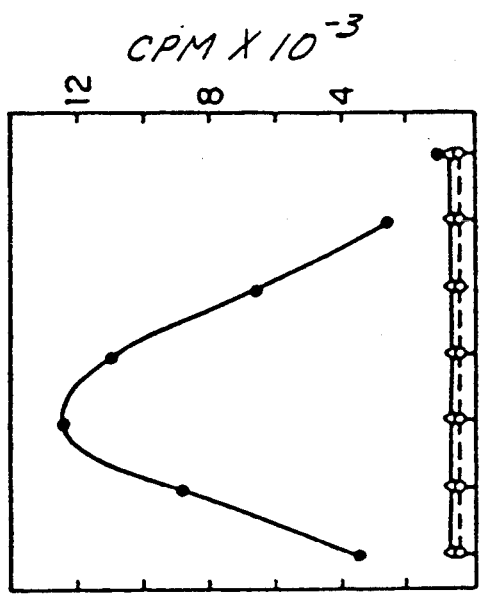
Figure 2C:
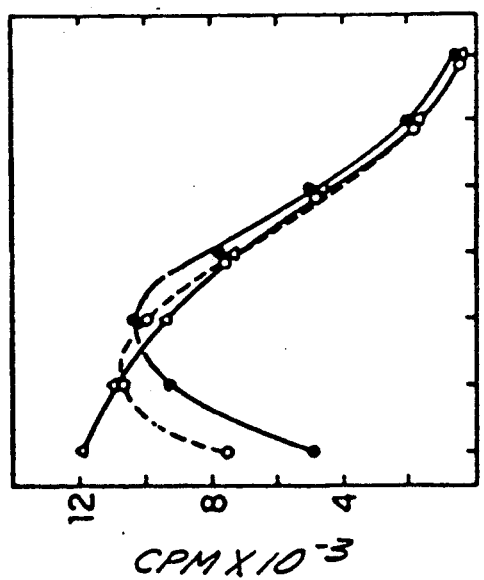

Referring to FIG. 1D and FIG. 2D, a remarkable selective reactivity with trifucosylated and difucosylated type 2 chain was observed for the antibody FH4, which did not react with monofucosylated type 2 chain $V^3$FucnLc$_6$, $VII^3$FucnLc$_8$, or $III^3$FucnLc$_4$. The antibody FH4, however, did not discriminate between di- and trifucosylated type 2 chain glycolipids.

Figure 2F:
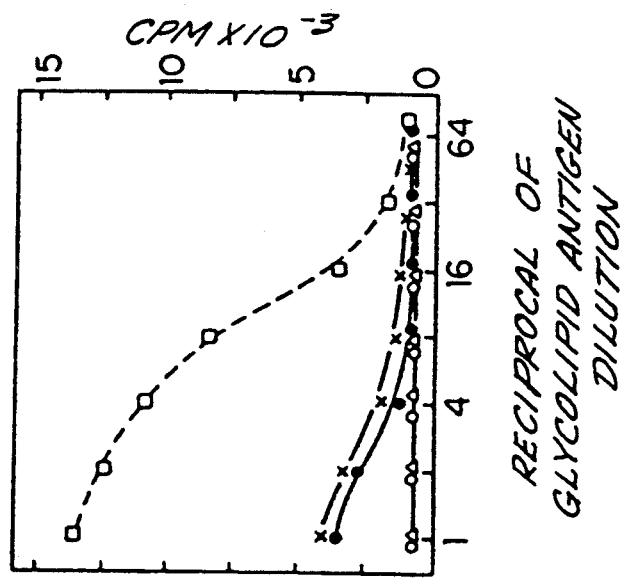
Figure 2E:
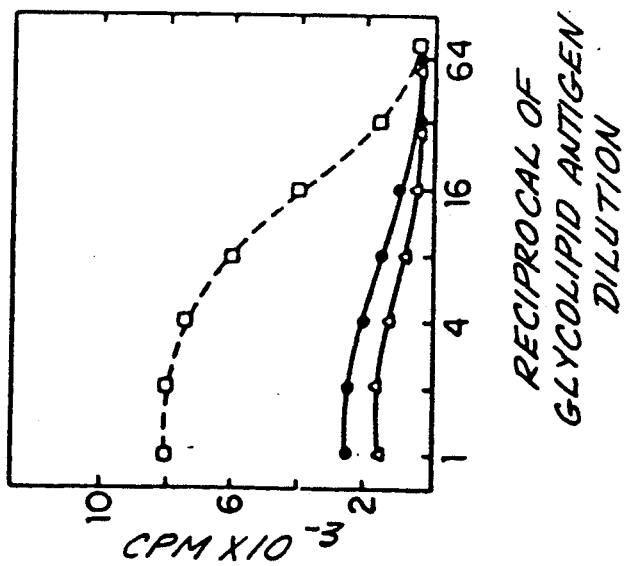

Referring to FIG. 1E and FIG. 2E, the antibody FH5 showed a preferential reactivity with trifucosylated neolactonoroctaosylceramide, but a cross-reaction with di- and monofucosyl neolactonorhexaosylceramide was observed. The antibody FH5 did not cross-react with lactofucopentaosyl(III)ceramide.

Referring to FIG. 2F, a similar, but more obvious, preferential reactivity with trifucosyl neolactonoroctaosylceramide was observed for the antibody clone ACFH18, which did not react with monofucosyl neolactonorhexaosylceramide or neolactonoroctaosylceramide (y$_2$; z$_1$) or lactofucopentaosyl(III)ceramide. The antibody ACFH18, however, cross-reacted minimally with difucosyl neolactonorhexaosylceramide.

Referring to FIGS. 1, A-E, and specifically to the lines with solid triangles therein, none of the above-stated FH series and ACFH18 monoclonal antibodies reacted with a glycolipid having an internal fucosyl residue ($III^3$FucnLc$_6$; Formula c, Table I) which was obtained by desialylation of a unique ganglioside. *Biochem. Biophys. Res. Commun.* 113: 791-798 (1983).

None of the above-stated FH series and ACFH18 antibodies reacted with glycolipids carrying the H structure (*Biochem.* 14: 2725-2733, 1975), specifically the H$_2$ glycolipid structure (Formula f, Table I), even in high concentration (2 μg/well) (data not shown).

Confirmation of the preferential reactivity of FH4 with difucosyl neolactonorhexaosylceramide The preferential reactivity of FH4 with difucosyl neolactonorhexaosylceramide was confirmed by inhibition of antibody binding to solid phase glycolipid-lecithin-cholesterol on vinyl strips. Solid phase radioimmunoassay was performed on a detachable vinyl strip as referenced above. The reactivity of FH3 and FH4 to the solid phase $III^3V^3$Fuc$_2$nLc$_6$ coated on a vinyl strip with cholesterol and lecithin was inhibited by liposomes containing $III^3V^3$Fuc$_2$nLc$_6$ or $V^3$FucnLc$_6$. The initial concentration of inhibitory glycolipid in liposomes was 1 μg/well. The glycolipid concentration on vinyl strips was 10 ng with 50 ng of lecithin and 30 ng of cholesterol/well. The concentration of antibody was a 1:50 dilution of the culture supernatant.

Figure 3A:
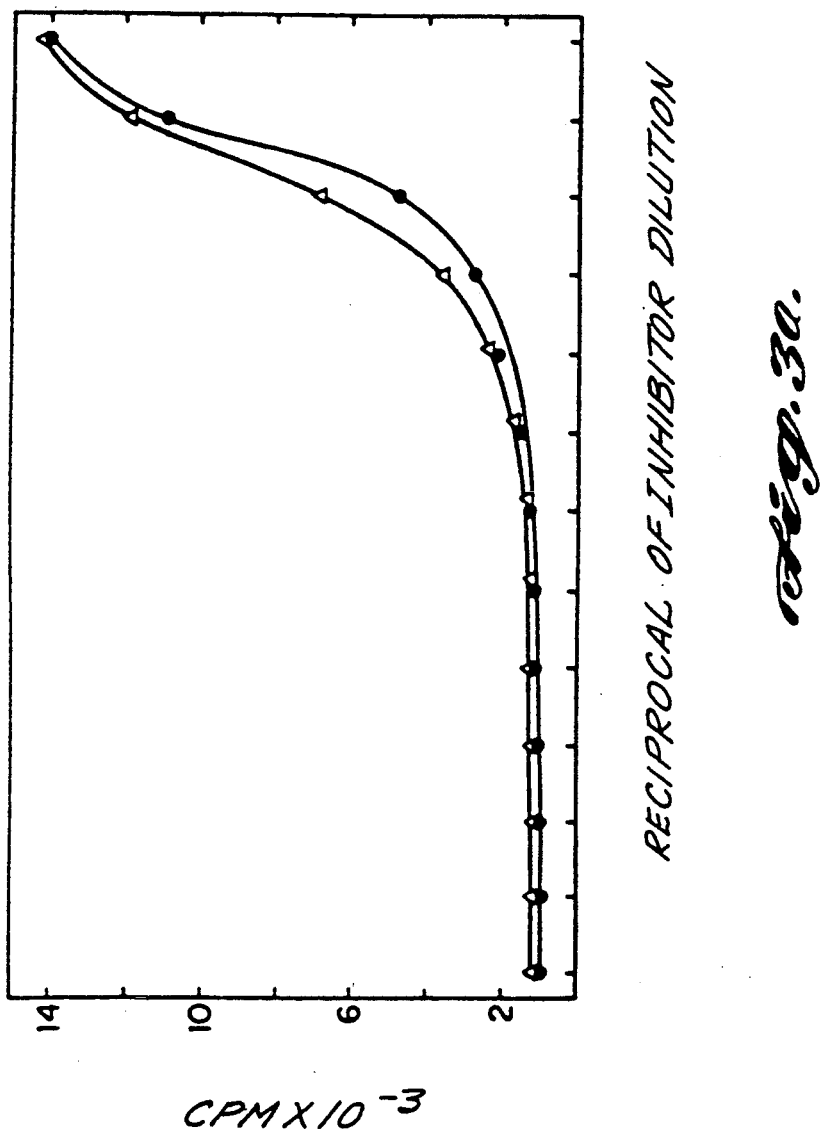
FIG. 3 is a pair of graphs that show the inhibition of the reactivity of FH3 and FH4 by glycolipid liposomes in solid phase radioimmunoassay, wherein graph A shows inhibition of the reactivity of antibody FH3 to III$^3$V$^3$Fuc$_2$nLc$_6$ by liposomes containing III$^3$V$^3$Fuc$_2$nLc$_6$ (●) and by liposomes containing V$^3$FucnLc$_6$ (△), and wherein graph B shows inhibition of the reactivity of antibody FH4 to III$^3$V$^3$FucnLc$_6$ by liposomes containing III$^3$V$^3$Fuc$_2$nLc$_6$ (●) and by liposomes containing V$^3$FucnLc$_6$ (△)
Figure 3B:
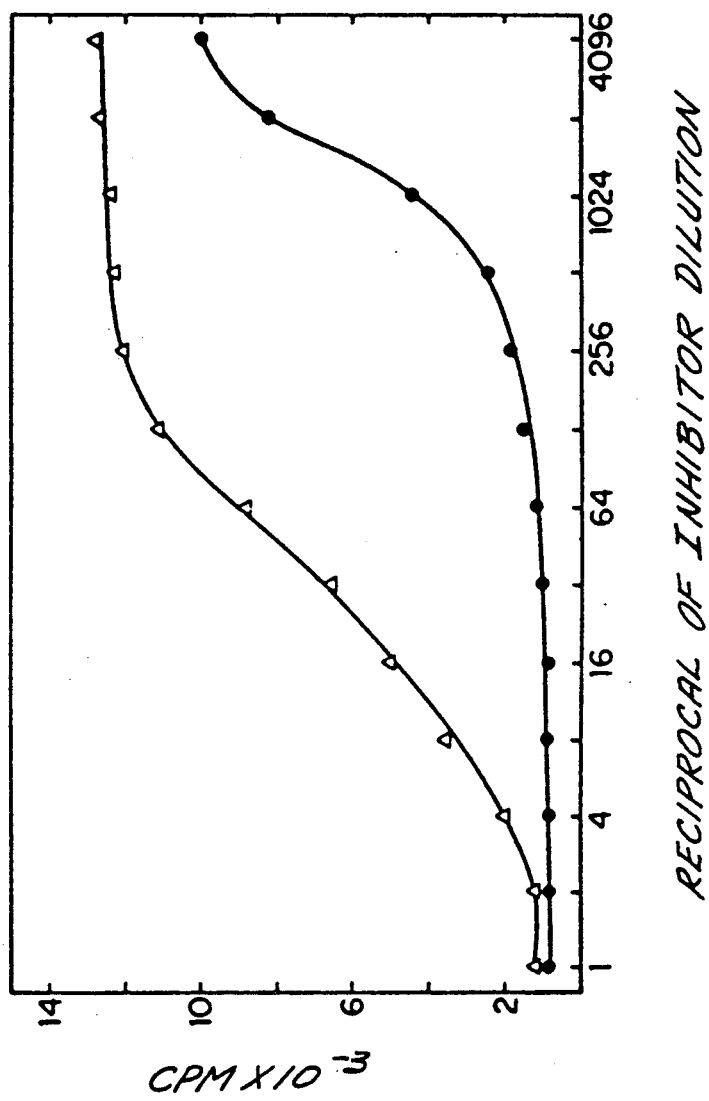

Referring to FIG. 3, the reactivity of the FH4 antibody with the solid phase difucosyl neolactonorhexaosylceramide was specifically inhibited by incubation of the antibody with the same glycolipid antigen in liposome.

Figure 4A:
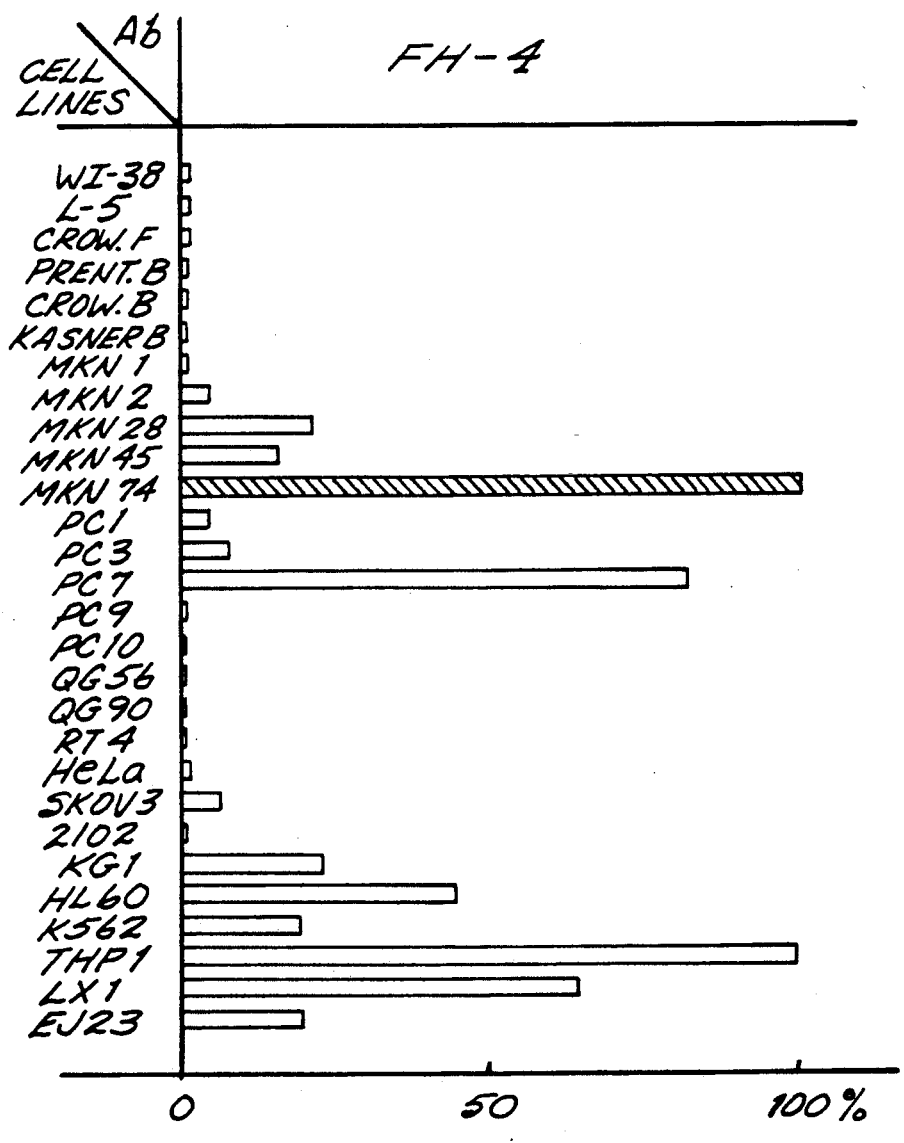
FIG. 4 is a pair of bar graphs that compare the reactivity of FH4 antibody and SSEA-1 antibody with various cell lines, wherein the reactivities of the various cell lines listed in the specification are expressed relative to that of gastric cell line MKN74 which is shown as a shadowed bar and is regarded as 100% in both graphs.
Figure 4B:
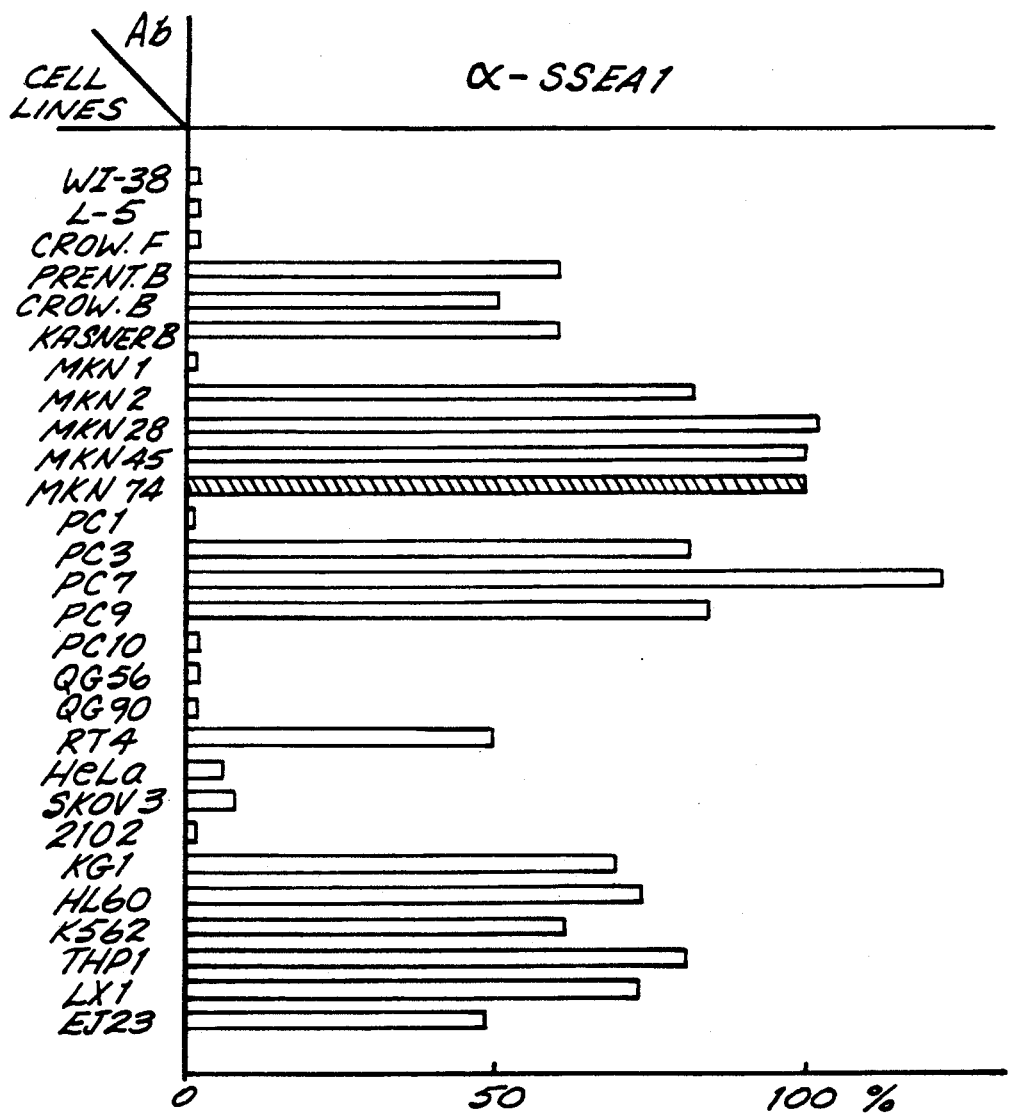

The selective reactivity of FH4 with certain types of tumor cells in contrast to an antibody directed to the X determinant The reactivity of FH4 was further tested with various cell lines in comparison to anti-SSEA-1, which recognizes the X determinant irrespective of the internal structure. *Biochem. Biophys. Res. Commun.* 100: 1578-1586 (1981); *Proc. Natl. Acad. Sci. U.S.A.* 75: 5565-5569 (1978); *Nature (Lond.)* 292: 156-158 (1981). As shown in FIG. 4, the reactivity of FH4 was much more restricted than that of anti-SSEA-1.

The cell lines listed on the ordinate of FIG. 4 were of the following types: gastric cancer cell lines MKN series (*Acta Med. Biol.* 27: 49-63, 1979); lung cancer cell lines QG-56, QG-90, PC-1, 3, 7, 9, and 10 (*Tampakushitsu-Kakusan-Koso (Protein-Nucleic Acid-Enzyme)* 23: 697-711, 1978); epidermoid tumor cells RT-4; ovarial adenocarcinoma SK-OV3 (*J. Natl. Cancer Inst.* 59: 221-226, 1977); monocytic leukemia cell line THP-1 (*Int. J. Cancer* 26: 171-176, 1980); myelocytic leukemia KG-1; erythroleukemia K562; B cell lines Prent, Crow, and Kasner; human fibroblasts WI-38 and L-5; human lung cancer cell line LX-1; human cervical carcinoma HeLa; human teratocarcinoma 2102; promyelocytic leukemia HL60; and human bladder carcinoma cell line EJ-23.

PC-7, PC-9, KG-1, HL-60, K562, THP-1, and B cell lines were cultured in suspension in RPMI 1640 medium supplemented with 10% fetal calf serum. All other cell lines were cultured in Dulbecco's modified Eagle's medium supplemented with 10% fetal calf serum. Trypsinized cells were washed and resuspended in phosphate-buffered saline, and $5 \times 10^4$ cells/well were seeded in Linbro plates which were precoated with 0.5 mg/ml of polylysine. Plates were centrifuged, and cells were fixed with 0.1% glutaraldehyde and used for antibody-binding assay.

The reactivity was expressed relative to that of gastric cancer cell line MKN74 which is shown as a shadowed bar in FIG. 4 and is regarded as 100%. Cells fixed on plates were treated with 5% bovine serum albumin in phosphate-buffered saline, pH 7.4, for 1 h, followed by incubation for 18 h with FH4 or anti-SSEA-1. Both antibodies were ascites form and 100 times diluted. The cells on plates were then successively treated with the second antibody followed by $^{125}$I-labeled protein A as described in *Cancer Res.* 43: 4997-5005 (1983). The second antibody for FH4 was 1000 times diluted rabbit antibody directed to mouse IgG$_3$, and that for anti-SSEA-1 was 1000 times diluted rabbit antibody directed to mouse IgM.

Referring to FIG. 4, a selective reactivity of FH4 with certain types of tumor cells, including gastric cancer cell line MKN74, lung cancer cell line PC-7, and monocytic leukemia cell line THP-1, was observed, in contrast to anti-SSEA-1 which reacts with a large variety of cells including nonmalignant B cell lines.

DISCUSSION

The carbohydrate structure with the X determinant, in either glycoproteins or glycolipids, is highly immunogenic in mice. Since the established Kohler-Milstein procedure depends solely on immunization of mice with cells, a great number of monoclonal antibodies, originally claimed to be "tumor-specific," have been found to be directed to the X determinant, i.e., Gal$\beta$1→4-[Fuc$\alpha$1→3]GlcNAc$\beta$1→R. The first monoclonal antibody indentified as being directed to this X determinant was anti-SSEA-1. *J. Biol. Chem.* 257: 14865-14874 (1982); *Proc. Natl. Acad. Sci. U.S.A.* 75: 5565-5569 (1978); *Nature (Lond.)* 292: 156-158 (1981). With the anti-SSEA-1 reagent a number of glycolipids with the X determinant have been detected in normal and tumor tissue. However, some adenocarcinomas accumulate lactofucopentaosyl(III) ceramide, difucosyl neolactonorhexaosylceramide, and trifucosyl neolactonoroctaosylceramide. These structures were not detected in normal erythrocytes, granulocytes, normal colonic mucosa, or normal liver, although various other bands with X determinant structure are present in those normal cells and tissues. Granulocytes are particularly rich in glycolipids with the X determinant. *Eur. J. Immunol.* 13: 306-312 (1983); *Blood* 61: 1020-1023 (1983); *Dev. Biol.* 93: 54-58 (1982).

In order to distinguish among various structures with fucosylated type 2 chain, hybridoma cell lines have been selected by a chemically well defined structure rather than by cells. For example, the hybridoma producing antibody FH4 was obtained by immunization with pure difucosyl neolactonorhexaosylceramide and selection by various purified glycolipids as listed in Table I. As a result, monoclonal antibodies directed to defined structures, and specifically those that can distinguish between mono- and di- and trifucosylated type 2 chain structures, were selected. The antibody FH4 is only reactive with di- and trifucosylated type 2 chain, but is not reactive with neolactonorhexaosylceramide that is monofucosylated at either the $V^3$ or $III^3$ positions. Namely, the antibody FH4 recognizes two adjacent fucosyl structures at the $III^3$ and $V^3$ positions. The antibody FH4 shows a preferential reactivity with some human tumor cell lines and shows no reaction with various B cell lines which were highly reactive with anti-SSEA-1. The restricted reactivity demonstrated by antibody FH4 indicates a restricted distribution of such structures with adjacent fucosyl residues in the type 2 chain. It is assumed that the structures could be synthesized by a mechanism of type 2 chain elongation coupled with $\alpha$1→3 fucosylation at every GlcNAc residue, as discussed in *J. Biol. Chem.* 259: 4672-4680 (1984). In contrast to the specificity of the FH4 antibody, the FH5 and ACFH18 monoclonals showed a preferential reactivity to trifucosylated type 2 chain (trifucosyl neolactonorhexaosylceramide), although a cross-reaction with difucosylated type 2 chain was also observed. Therefore, the monoclonal antibodies FH4, FH5, and ACFH18 are specific reagents that recognize di- or trifucosyl residues linked to type 2 chain, excluding the terminal X-hapten structure.

A possible epitope recognized by the FH series, ACFH18, and previously established monoclonals directed to the X determinant is shown in FIG. 5. Various monoclonal antibodies including FH2 and FH3 are directed to X determinant, in contrast to FH1 which recognizes internal repeating type 2 chain as well. FH4 recognizes two fucosyl residues (shown as a solid zone), and FH5 and ACFH18 recognize three fucosyl residues (shown as shadowed zone) linked to type 2.

It is predicted that these antibodies will be useful in detecting specific types of cells such as tumor cells and undifferentiated cells that are characterized by enrichment in di- or trifucosylated type 2 chain structure of human cancer. In order to evaluate this possibility the following experiments were performed.

SECOND SERIES OF EXPERIMENTS

Because it was noticed that the di- or trifucosylated type 2 chains (or multimeric X antigens) defined by antibody FH4 were much more restricted than the X hapten structure defined by FH3, and because both FH3 and FH4 antibodies are IgG3 with comparable reactivities, a systematic study of the distribution of the antigens defined by these two antibodies in various stages of human development and in human cancer in comparison with adult normal tissues was undertaken using immunohistological techniques. Tissue sections were stained by monoclonal antibody FH3, which defines X determinant, and by monoclonal antibody FH4, which defines di- or trimeric X determinant. The following general trends in the expression of the antigens defined by FH3 and FH4 have been observed: (a) A well-organized, orderly appearance and disappearance of the antigens was observed during the histogenesis of various epithelia of gastrointestinal and other organs. The development stage exhibiting the maximum antigen expression is different for each organ. (b) The X determinant defined by FH3 is expressed about 2 wk earlier than the di- or trimeric X determinant defined by FH4, and the antigen defined by FH4 regressed more rapidly and more completely than the X determinant defined by FH3 on further development of epithelial tissue. Thus, expression of the FH4 antigen is highly limited to specific types of cells in newborn and adult epithelial tissues. (c) The antigen defined by FH4 was strongly expressed in the majority of tubular and papillary adenocarcinoma of stomach, adenocarcinoma of colon, and infiltrating ductal carcinoma of breast and its metastatic lesions. No antigen defined by FH4 was found in poorly differentiated stomach adenocarcinoma, squamous lung carcinoma, and many other types of tumors from ovary, testis, prostate, skin, and muscle. The presence of the antigen defined by FH4 is therefore limited to carcinoma of the stomach, colon, and breast and can be regarded as a retrograde expression of the antigen to a certain stage of fetal development in which expression of this antigen was maximal.

Materials and Methods

Tissues. 27 human embryos and fetuses (aged 1-8 wk and 9-38 wk after fertilization, respectively) were collected at the Division of Human Embryology and Teratology, Department of Pediatrics, University of Washington. The ages of the embryos and fetuses were between 38 and 127 d, and were organized as described in *Monitoring Birth Defects and Environment: The problem of surveillance*. E. B. Hook, et al., eds., Academic Press, N.Y., pp. 29-44 (1971). Two newborn tissue samples were donated from the Department of Pathology, Children's Orthopedic Hospital, Seattle. Various normal adult tissues, including colon, stomach, ovary, lung, skin, breast, liver, spleen, and skeletal muscle, were obtained from specimens associated with the surgical removal of tumors. In total, 65 cases of various cancer tissues were obtained from the Department of Surgery, Swedish Hospital, Seattle, and from Japan Immunoresearch Laboratories, Takasaki, Japan. Formalin-fixed, paraffinembedded sections of normal bladder, urethra, and testis were obtained from the Department of Urology, Tohoku University School of Medicine, Sendai, Japan.

Antibodies. IgG3 monoclonal antibodies FH3 and FH4 were purified from culture supernatant or from ascites fluid by affinity chromatography on a protein A-Sepharose column. Antibody adsorbed on protein A-Sepharose was eluted with 0.1M citrate buffer, pH 4.2, dialyzed against phosphate-buffered saline (PBS: 10 mM sodium phosphate buffer, pH 7.2, containing 0.9% NaCl), and stabilized by addition of 0.1% bovine serum albumin. The final concentration of antibody was adjusted to 100 µg/ml, which was approximately equivalent to a sixfold dilution of ascites. The secondary antibody (rabbit Ig directed to mouse Ig) conjugated with horseradish peroxidase was purchased from Accurate Chemicals Co., Westbury, NY.

Preparation of Tissue Sections. Tissues were embedded in OCT compound (Tissue-Tek II Division, Miles Laboratories, Inc., Naperville, IL), frozen in dry ice-acetone, and stored in a Revco freezer at −80° C. until use. Frozen sections (4–6 µm thick) were prepared on a cryostat. Each section was dried on objective glass for 30 min at room temperature, fixed in acetone at 4° C. for 10 min, and washed with PBS at 4° C. Tissue sections (6–8 µm thick) were also prepared from formalin-fixed, paraffin-embedded specimens according to established procedure. Sections were deparaffinized in xylene for 5 min at 4° C., dehydrated in ethanol, and washed with PBS. Before antibody labeling, frozen sections and paraffin-embedded sections were blocked by incubation with 15% normal rabbit serum in PBS for 1 h at room temperature.

Immunostaining Procedure. After blocking with normal rabbit serum, sections were incubated at room temperature with the primary antibody solution (FH3 or FH4 as prepared above) for 18 h in a moist chamber. Sections were washed three times with PBS at 4° C. (5 min per washing). Sections were then incubated with the peroxidase-conjugated secondary antibody (diluted 1:30) for 1 h at room temperature in a moist chamber and washed three times in PBS at 4° C. as above. Bound antibodies were detected by incubating tissue sections in 0.05M Tris/HCl buffer, pH 7.6, containing 0.03% 3,3′-diaminobenzidine (Sigma Chemical Co., St. Louis, MO) and 0.008% hydrogen peroxide. After 10 min, the sections were washed with distilled water, counter-stained with hematoxylin, dehydrated in ethanol, washed with xylene, and mounted.

Two controls were performed for each staining experiment: sections treated without the primary antibody and sections treated with normal mouse serum. Specific tissue labeling was not observed after either of the above control treatments.

Comparison of Immunostaining of Frozen Sections and Paraffin-Embedded Sections. In view of a possible deletion of glycolipid antigens during preparation of sections from paraffin-embedded specimens, staining of the antigens in these sections was carefully compared with cryostat sections from frozen samples. There were no significant differences in immunoreactivity between frozen sections and paraffin sections for both fetal and newborn specimens.

General developmental changes of antigens defined by FH3 and FH4 antibodies

Strong staining of embryonic and fetal tissue by both FH3 and FH4 antibodies was limited to gastrointestinal and urogenital epithelia, and the patterns of antibody reactivity showed dramatic changes depending on the stage of the embryo. The X determinant defined by the FH3 antibody showed a wider distribution than the multimeric X antigen defined by the FH4 antibody. Both antigens were absent or present in relatively low concentration during early embryonic development (up to 40–50 d), showed maximum expression at a specific stage of development (mostly 50–70 d), and regressed upon further differentiation and development. The antigen defined by FH3 appeared about 2 wk earlier than the antigen defined by FH4 and either regressed later than that defined by FH4 or was continuously expressed after birth. Thus, the FH4 antigen was often limited to a specific type of cell in certain epithelial tissues, as discussed further below.

Weak staining was also observed in the pulmobronchial epithelia, adrenal medulla, and entire layers of the epidermis by both FH3 and FH4 in embryonic stages. The reactivities of FH4 regressed completely in newborn tissues. A weak staining with FH3 remained, however, in the adrenal medulla as well as in sebaceous and sweat glands of the epidermis.

The antigens recognized by FH3 and FH4 were not found in connective tissues, nervous tissues (brain and spinal cord), tissues of the circulatory system (heart, arteries, and veins), skeletal tissue (bones and muscles), or other parenchymatous organs, such as liver and spleen, at any stage of development. Distribution of the antigen defined by FH4 in tissues of newborns and adults was limited to specific types of cells in gastric and intestinal epithelia, and the antigen was completely absent in colonic epithelia.

The reactivities of the FH3 and FH4 antibodies with fetal, newborn, and adult tissues are summarized in Tables II, III, and IV.

TABLE II

| | | Reactivities of Digestive Organs of Human Embryo with FH3 and FH4 | | | | | | | | | | | | |
|---|---|---|---|---|---|---|---|---|---|---|---|---|---|---|
| | | Stages of embryo (in days of gestation) | | | | | | | | | | | | |
| Antibody | Organ | 38 P* | 40 F§ | P | 42 P | 52 F | 53 P | 53 P | 54 F | P | P | 57 P | 58 P | 59 P | 67 F |
| FH3 | Esophagus | + | − | | | | | | | + | | | | + | |
| | Stomach | ++ | ++ | ++ | ++ | | | | ++ | ++ | | | | ++ | |
| | Small intestine | + | − | − | | | | | ++ | ++ | | − | + | + | + | −,++ |
| | Colon | ± | − | | | ± | | + | ± | ± | | | | − | − |
| | Liver | | | | | | | | | | | | − | | |
| | Gall bladder | | | | | | | | | | | | ± | | |
| | Pancreas | ± | − | | + | ± | | | ± | | | | | − | |

TABLE II-continued
Reactivities of Digestive Organs of Human Embryo with FH3 and FH4

| | | | | | | | | | | | | | | |
|---|---|---|---|---|---|---|---|---|---|---|---|---|---|---|
| FH4 | Esophagus | − | − | | | | | ± | | − | | | | |
| | Stomach | ++ | ++ | ++ | ++ | | | ++ | ++ | | | ± | ++ | |
| | Small intestine | − | − | − | | | − | ± | − | ± | ++ | + | −,++ | |
| | Colon | − | − | | | − | + | − | + | | | − | ± | |
| | Liver | | | | | | | | | − | | | | |
| | Gall bladder | | | | | | | | | ± | | | | |
| | Pancreas | − | − | | − | | | ± | | | | − | | |

| | | Stages of embryo (in days of gestation) | | | | | | | |
|---|---|---|---|---|---|---|---|---|---|
| | | | 69 | 72 | 84 | | 110 | 127 | Newborn |
| Antibody | Organ | P | F | F | F | P | P | P | P | P |
| FH3 | Esophagus | | | | | | | | + | + |
| | Stomach | | ++ | | ++ | ++,+ | | −,+§ | −,+,++ | −,+,++ |
| | Small intestine | + | −,+ | −,+ | −,+ | −,+ | −,± | −,+ | −,++** | −,++** |
| | Colon | | ± | | | | | | − | − |
| | Liver | | | − | | | | | − | |
| | Gall bladder | | | | | | | | | |
| | Pancreas | | | | | | | ± | | −,± |
| FH4 | Esophagus | | | | | | | | ± | − |
| | Stomach | | ++ | | ++ | ++ | + | −,+§ | −,+,++ | −,+,++ |
| | Small intestine | + | −,+ | −,++ | −,++ | −,+ | −,± | −,+ | −,++** | −,++** |
| | Colon | | − | | | | | | − | − |
| | Liver | | | − | | | | | | |
| | Gall bladder | | | | | | | | | |
| | Pancreas | | | | | | | | − | − |

*Paraffin section.
§Frozen section.
§+, Deeply folded portion; −, superficial portion.
−, chief cells; +, surface mucous cells; ++, parietal cells and other epithelial cells.
Some unidentified cells are strongly positive.
**++, Paneth's cell, basal granular cells; −, other epithelial cells.
±, Cells of Islets of Langerhans; −, other cells.

TABLE III
Reactivities of Circulatory, Respiratory Organs, Adrenal, Skin, and Nervous System of Human Embryo with FH3 and FH4 Antibodies

| | | Stage of embryo (in gestation days) | | | | | | | | | | | | | | | | | | |
|---|---|---|---|---|---|---|---|---|---|---|---|---|---|---|---|---|---|---|---|---|
| | | 38 | 40 | 52 | 53 | 54 | | 58 | 59 | 64 | 67 | 69 | 72 | | 84 | 110 | 127 | Newborn | |
| Antibody | Organ | P | F | F | P | F | P | P | P | P | F | F | P | F | P | P | P | P | F |
| FH3 | Heart, artery and vein | − | − | − | − | − | − | | − | | | | | | | | | − | − | |
| | Lung airway | | | | | + | + | | − | | | − | ± | ± | | | − | − | | |
| | Trachea | | | | | | | | | | | | | | + | | + | + | | |
| | Cerebrum, cerebellum and pons | | | − | − | | | | | | | | − | − | | | − | | − | |
| | Spinal cord | − | − | − | − | | | | | | | | − | − | | | | − | − | |
| | Adrenal | − | − | | | − | −,±* | −,±* | −,±* | −,+* | −,±* | | −,±* | | −,±* | | | −,± | | |
| | Spleen | | | | | | | | | | | | | | | − | | − | | |
| | Skin | +§ | | | +§ | | +§ | | +§ | | | | | | | | | | + | |
| | Bone and Muscle | − | − | − | | | − | − | | | | | | | | − | | | | |
| FH4 | Heart, artery and vein | − | − | − | − | − | − | | − | | | | | | | | | − | − | |
| | Lung airway | | | | | − | ± | | − | | | − | − | | | | − | − | | |
| | Trachea | | | | | | | | | | | | | | + | | ± | − | − | |
| | Cerebrum, cerebellum and pons | | | − | − | | | | | | | | −, | − | | | − | | − | |
| | Spinal cord | − | − | | | | | | − | | | | − | − | | | | − | − | |

TABLE III-continued

Reactivities of Circulatory, Respiratory Organs, Adrenal, Skin, and Nervous System of Human Embryo with FH3 and FH4 Antibodies

| Anti-body | Organ | Stage of embryo (in gestation days) | | | | | | | | | | | | | | | | Newborn | |
|---|---|---|---|---|---|---|---|---|---|---|---|---|---|---|---|---|---|---|---|
| | | 38 | 40 | 52 | 53 | 54 | | 58 | 59 | 64 | 67 | 69 | 72 | | 84 | 110 | 127 | | |
| | | P | F | F | P | F | P | P | P | P | F | F | P | F | P | P | P | P | F |
| | Adrenal | − | − | − | | − | −,±* | −,± | −,±* | −,± | −,±* | | −,±* | −,±* | | | | −.±* | |
| | Spleen | | | | | | | | | | | | | | | | | | |
| | Skin | +§ | | +§ | | +§ | | | +§ | | | | | | − | | | − | − |
| | Bone and muscle | − | − | − | − | | − | − | | | | | | − | | | | − | |

*Adrenal cortex, −; medulla, ±.
 Adrenal cortex, −; medulla, +.
§Entire layers of skin, +.
 Duct of ecrine sweat gland, +; epidermis, +; corium, −.
 Entire layer, −.

TABLE IV

Reactivities of Human Adult Tissues with FH4 Antibody

| Tissue | Reactivity (number of cases) | |
|---|---|---|
| | Paraffin section | Frozen section |
| Stomach | | |
| Surface mucous cells | −,±* | ± |
| Chief cells | − | − |
| Parietal cells | + + (4) | + (3) |
| Pyrolic gland | + + | + |
| Other cells | −,+ | ± |
| Small intestine | | |
| Paneth's cells | + + | + + |
| Basal granular cell | + + | + + |
| Cuticular or brush border cells | − (2) | − (1) |
| Globlet cell | − | − |
| Colon | | |
| Crypt cells | − | −,+§ |
| Cuticular cell | − (4) | −, (7) |
| Globlet cells | − | −. |
| Mammary gland | | |
| Parenchyma and duct cells | − (3) | − (4) |
| Lung | − (3) | − (4) |
| Skin | − (2) | − (1) |
| Testis | − (3) | |
| Prostate | − (4) | |
| Muscle | | − (2) |

A single grading indicates that all cases examined showed the same degree of reactivity.
*−, Three of four cases; ±, one of four cases.
 −, Three of four cases; +, one of four cases.
§−, Six of seven cases; +, one of seven cases.

Figure 6:
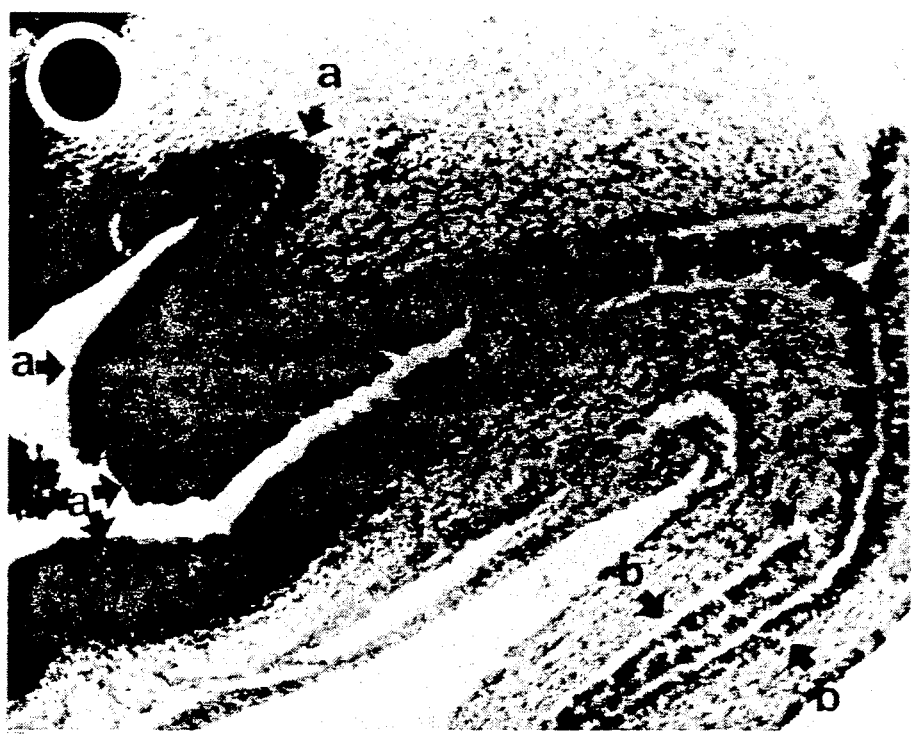
FIG. 6 is a photomicrograph of a paraffin-embedded section of gastric and intestinal tissue of the foregut of a 38-d-embryo stained by antibody FH4, wherein arrows a indicate gastric epithelia (strongly stained by FH4) and arrows b indicate intestinal epithelia (not strongly stained by FH4)
Figure 7:
FIG. 7 is the same as FIG. 6 except stained by antibody FH3, which strongly stains both gastric and intestinal epithelia.
Figure 8:
FIG. 8 is a paraffin-embedded section of gastric epithelia of 120-d-old fetus stained by FH4, wherein arrows a indicate deep foveola (strongly stained by FH4)
Figure 9:
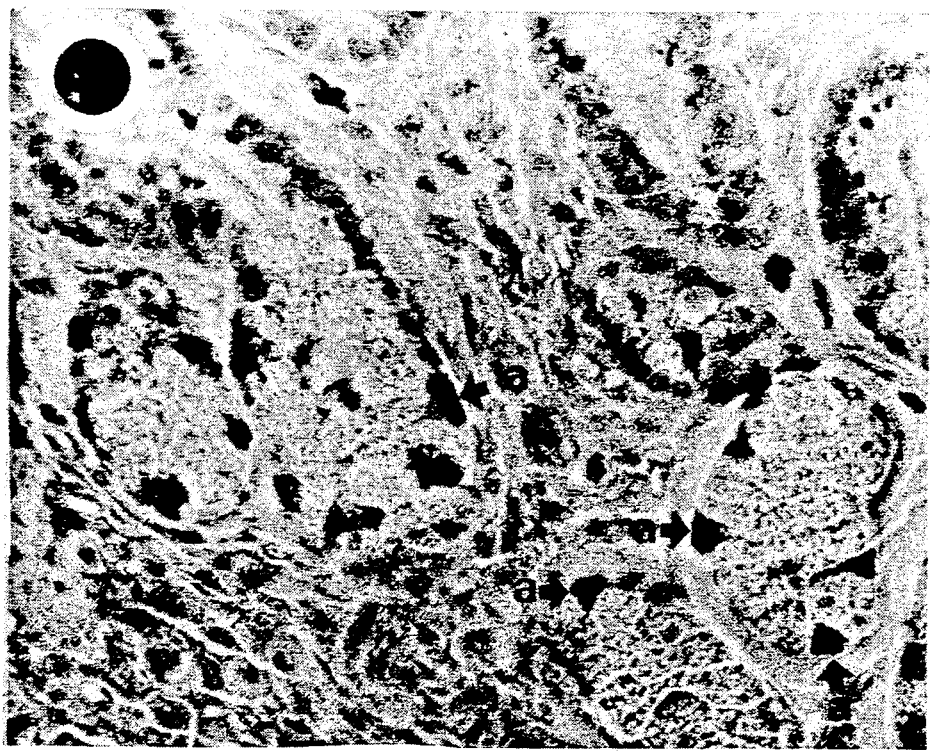
FIG. 9 is a paraffin-embedded section of newborn intestinal epithelia stained by FH4, showing the majority of cells are negative and only Paneth's cells and basal granular cells (arrows a) are stained.

Distribution of antigens defined by FH3 and FH4 antibodies in gastrointestinal tissues of the human embryo The strongest expression of the antigens defined by FH3 and FH4 antibodies was found in stomach epithelia. The reactivity was intense in all cell populations of stomach epithelia at 35 d of development (FIGS. 6 and 7, arrows a). This intense reactivity continued up to 90 d. After 100 d, the reactivity of many stomach cell populations regressed, became limited to a deep layer at later stages (FIG. 8, arrows a), and was finally limited to the parietal cells (FIG. 9, arrows a) and pyloric glands (data not shown) of newborn and adult gastric epithelia. The chief cells and other epithelial cells in stomach epithelia became completely negative in newborn and adult epithelia (see Table IV and FIG. 9).

Figure 10:
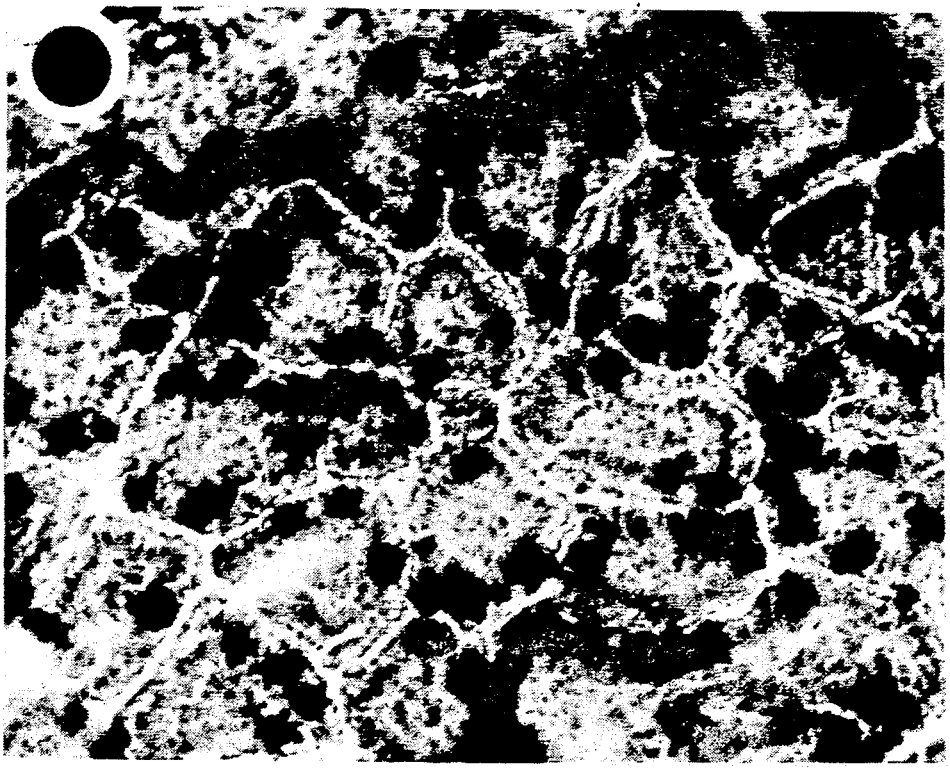
FIG. 10 is a paraffin-embedded section of intestinal epithelia of 70-d-old fetus stained by FH4, showing many groups of cells (not indentified exactly) are strongly stained, but unstained cells can also be seen.
Figure 11:
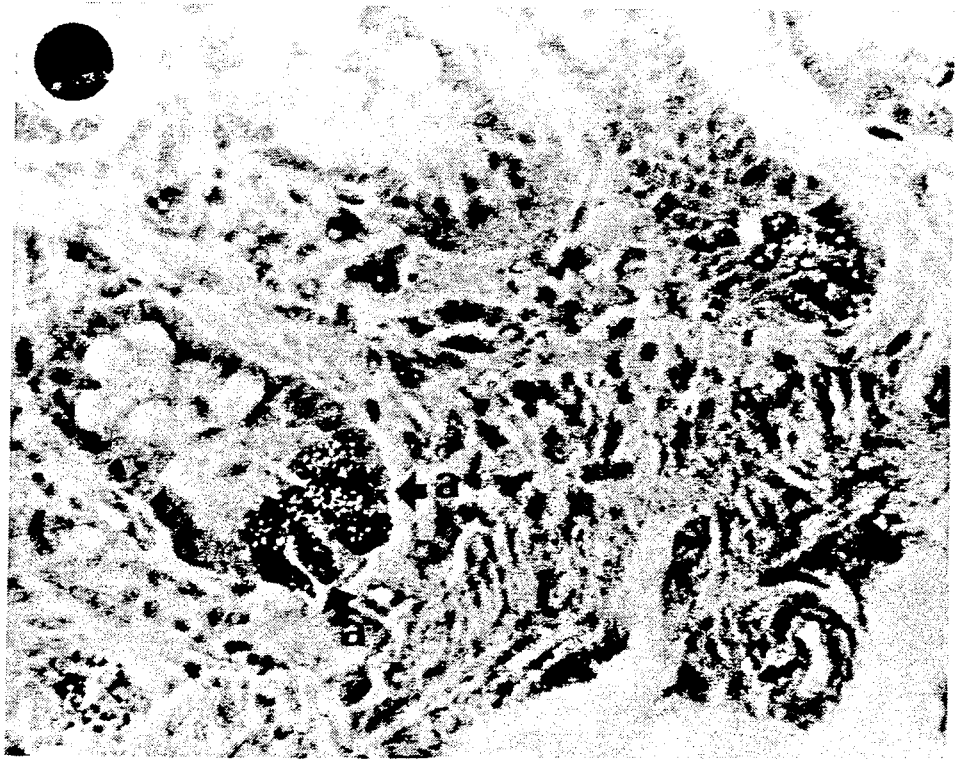
FIG. 11 is a paraffin-embedded section of newborn intestinal epithelia stained by FH4, showing the majority of cells are negative and only Paneth's cells and basal granular cells (arrows a) are stained.

Small intestinal epithelial cells were not stained by FH4 at 40 d of development (FIG. 6, arrows b) but were strongly stained by FH3 (FIG. 7, arrows b). At later stages, the majority of small intestine epithelial cells became negative; however, a strong reactivity with both FH3 and FH4 was observed in some unidentified cells of fetal tissue (FIG. 10). The antigens defined by both FH3 and FH4 in the majority of cell populations regressed subsequently, becoming restricted only to Paneth's cells and basal granular cells in the cryptic region of the newborn and adult small intestine (FIG. 11, arrows a; Table IV).

Figure 12:
Figure 13:
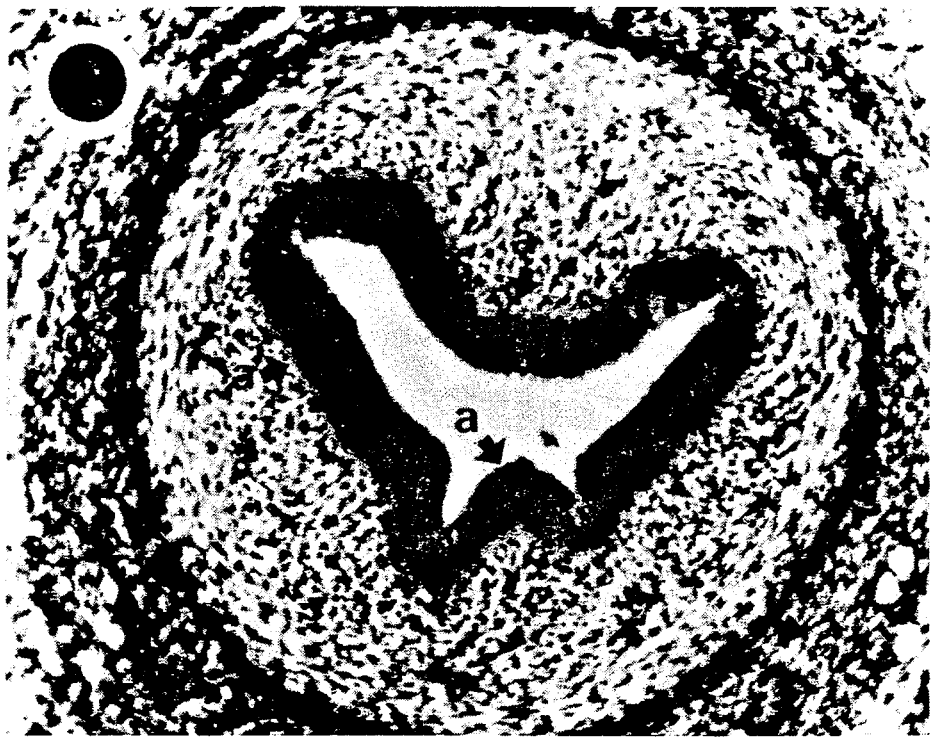
FIG. 13 is a frozen section of colonic tissue of 50-d-old embryo stained by FH3, showing only epithelial tissue (arrows a) is stained.
Figure 14:
FIG. 14 is a frozen section of adult colonic epithelia stained by FH3, showing crypt cells (arrows a) clearly stained.

The reactivity of FH3 and FH4 with colonic epithelial cells showed a similar pattern. These cells were weakly positive in the early embryo, became positive and maximally expressed between 50 and 60 d (FIG. 13, arrows a; the same section was not stained by FH4), and subsequently regressed. At later stages, FH3 antigen expression was limited to crypt cells in the newborn and adult (FIG. 14, arrows a; the same section was not stained by FH4). Crypt cells in newborn and adult tissues were not stained by FH4 (data not shown). The antigen defined by FH3 was present in esophageal epithelia in the early fetus (FIG. 12) as well as in the newborn and adult (data not shown), but the antigen defined by FH4 was absent in esophageal epithelia throughout all stages of embryonic development examined. A similar distribution was found in the fetal pancreas; the ductal epithelium was weakly stained by FH3, but not by FH4, and became completely negative in the newborn. It is interesting to note that the antigen defined by FH3 was present in cells of Langerhans' islets, but that defined by FH4 was absent (data not shown). Neither antigen was detected in the various stages of liver development (data not shown).

Respiratory organs and other tissues

The epithelial cells of trachea and secretory glands of bronchus were stained by FH3, but not by FH4 in newborns. No fetal tissue of bronchus was available. The epithelial cells of the lung airway found in fetal lung bud were positive with FH3, but were negative with FH4 (data not shown). The entire layer of epidermal tissue of fetal age was positive with both FH3 and FH4, but the reactivity with FH4 became negative in adult tissue. A weakly positive reaction was observed with FH3 in sebaceous glands and in ecrine sweat glands; no reactivity was observed with FH4 (data not shown). Heart, aorta, arteries, veins, cerebrum, cerebellum, pons, spinal cord, muscles, and bones were all negative with both FH3 and FH4 throughout all developmental stages (data not shown).

Distribution of the antigen defined by FH4 in human cancer in comparison with adult normal tissues

TABLE V

Reactivities of Human Cancers with FH4 Antibody

| Tumor Tissue | | Reactivity (number of cases) | |
|---|---|---|---|
| | | Paraffin section | Frozen section |
| Stomach cancer | Adenocarcinoma | ++ (5/11) | ++ (2/5) |
| | | + (3/11) | + (2/5) |
| | | − (4/11) | − (1/5) |
| Colon cancer | Adenocarcinoma | ++ (⅔) | ++ (⅝) |
| | | + (⅓) | + (2/8) |
| | | − (0/3) | — |
| Ovary | Clear cell carcinoma | | − (1/1) |
| | Serous cystoadenocarcinoma | | − (1/1) |
| | Mucinary cystoadenocarcinoma | | − (1/1) |
| Testis | Seminoma | − (3/3) | |
| Breast | Infiltrating ductal carcinoma | ++ (¾) | ++ (¾) |
| | | − (¼) | − (¼) |
| | Lymph node metastasis | ++ (2/2) | ++ (2/2) |
| Lung | Squamous cell carcinoma | − (2/2) | − (4/4) |
| Gall bladder | Adenocarcinoma | | + (1/1) |
| Prostate | Adenocarcinoma | − (3/3) | |
| | Benign adenoma | − (3/3) | − (1/1) |
| Skin | Malignant melanoma | − (1/1) | − (1/1) |
| Muscle | Leronmyosarcoma | − (1/1) | − (1/1) |
| | | | − (1/1) |

Figure 17:
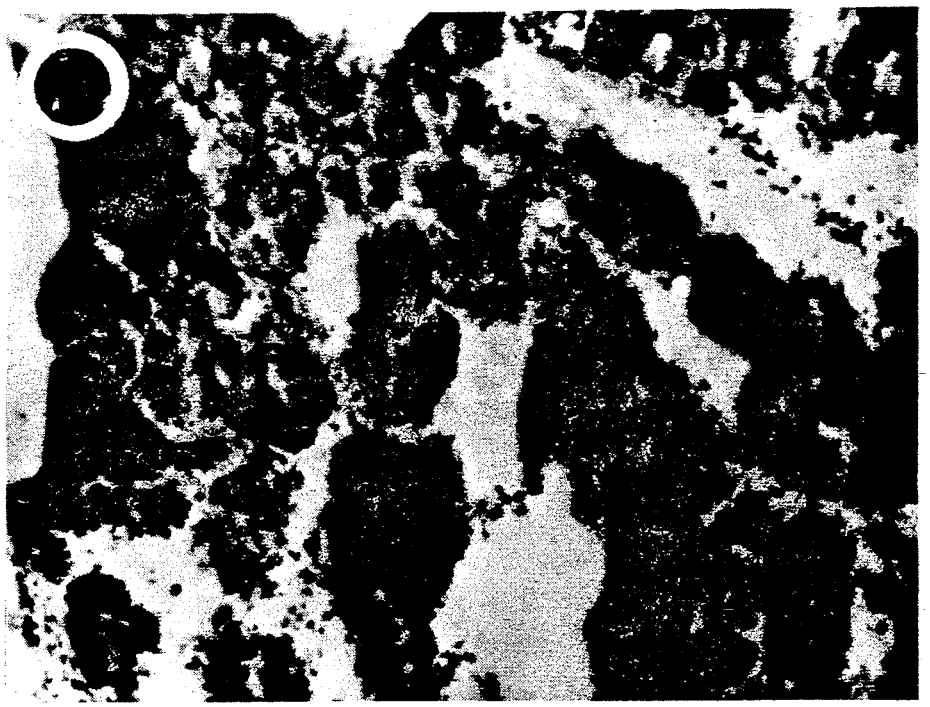
FIG. 17 is a frozen section of tubular adenocarcinoma of stomach stained by FH4.

Gastric cancer. 8 out of 11 cases of paraffin-embedded sections and four out of five frozen sections of gastric cancers were strongly or clearly positive with FH4 (see Table V). All the positive cases were tubular or papillary adenocarcinoma, while all the negative cases were undifferentiated adenocarcinoma (see Table V). A typical positive example is shown in FIG. 17. In normal adult gastric epithelia, only parietal cells and pyloric gland cells were consistently positive in both paraffin and frozen sections (see Table IV).

Figure 15:
FIG. 15 is a frozen section from adenocarcinoma of colon stained by FH4, showing stroma (a) not stained but heavy staining of tumor cells by FH4.

Colonic cancer. Three out of three cases of paraffin-embedded sections and seven out of eight cases of frozen sections were strongly or clearly positive with FH4 (see Table V). A typical section from colonic cancer is shown in FIG. 15. Only one case was negative, which was not correlated with the histological characteristics of the case. Normal parts of colonic epithelia were all negative, including crypt cells in both paraffin and frozen sections, except for one case that showed a positive reaction in the crypt cells.

Figure 16:
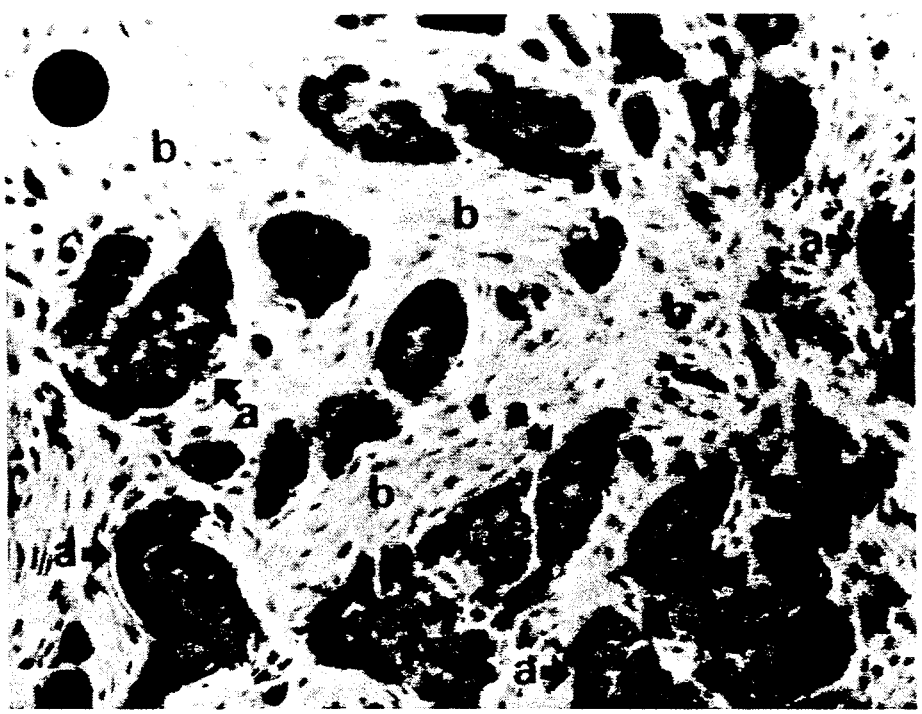
FIG. 16 is a frozen section from infiltrative ductal carcinoma of breast stained by FH4, showing only tumor cells (arrows a) but not stroma (b) are stained.

Breast cancer. Three out of four cases of both paraffin-embedded and frozen sections of infiltrating ductal carcinoma were positive with FH4. A typical case is shown in FIG. 16. Metastatic lesions in lymph nodes were also strongly positive (see Table V).

Kidney cancer. A great deal of variation in the staining of kidney tumors was observed, which may appropriately reflect the normal variation in the reactivity of FH3 and FH4 with urogenital epithelia during their development from pronephros to mesonephros to metanephros.

Other cancers. Various types of ovarial carcinoma, seminoma, lung squamous cell carcinoma, prostrate adenocarcinoma, malignant melanoma, and leiomyosarcoma were all negative with FH4.

DISCUSSION

The reactivity of FH3 and FH4 with the developing human embryo and fetus can be summarized as follows:

(a) The antigens detected by both FH3 and FH4 are most strongly expressed in the epithelial cells of the gastrointestinal and urogenital organs at specific stages of development. Expression of these antigens, particularly FH4, regressed upon further development with functional differentiation and disappeared from most of the epithelial cell populations of those tissues with the exception of a few specific types of cells in normal adult tissue. (b) The antigen defined by FH3 appeared at an earlier stage of fetal development than the antigen defined by FH4; however, the antigen defined by FH4 regressed rapidly and completely at later stages of development and its expression became highly limited in adult epithelial tissues. The antigen defined by FH3 remained in a wider variety of cells than the antigen defined by FH4 in developed tissues. (c) In adult epithelial tissue, the antigen defined by FH4 was found to be limited to parietal cells and pyloric glands of stomach epithelia, Paneth's cells and basal granular cells of the intestine, and proximal convoluted tubules of the kidney. The antigen was not detected by FH4 in the entire colonic epithelia, including crypt cells. The crypt cells in colonic epithelia were positive with FH3. (d) A clear differential reactivity was found between the FH3 and FH4 antibodies in sebaceous and sweat glands of the epidermis, Langerhans' islet of the pancreas, adrenal medulla, espphageal epithelia, bronchial epithelia, airway of lung buds, and vaginal epithelia. Cells in these tissues were clearly or strongly stained by FH3, but were not reactive with FH4 throughout fetal development as well as in newborn and adult tissues.

The antigens defined by FH3 and FH4 may not be expressed or may be expressed weakly in preimplantation human embryos, in contrast to mouse embryos. This possibility is suggested by the absence of SSEA-1 in undifferentiated human teratocarcinoma and its appearance on differentiation (*EMBO* (*Eur. Mol.Biochem. Org.*) J. 2: 2355, 1983), in contrast to a strong expression of SSEA-1 in undifferentiated mouse teratocarcinoma and its decline on differentiation (*Proc.Natl.Acad. Sci.U.S.A.* 75: 5565, 1978; *Dev. Biol.* 83: 391, 1981). There were no cases in which tissues were negative at fetal stages, followed by increasing expression in newborn or adult tissues.

Maximum expression of the antigens defined by FH3 and FH4 was found in the epithelia of tissues at a specific developmental stage, mostly 40–80 d. This may indicate that these structures are essential signals for cell adhesion and recognition, which could be an essential step for further differentiation of fetal epithelial cells into a variety of functionally differentiated adult epithelial cells. Despite our lack of knowledge of a functional role of these structures, such a dramatic change, with maximum expression at a defined stage followed by orderly disappearance, suggests a vital function for these structures in "chemical conversation" (*Dev. Biol.* 250, 1968) between embryonic cells during epitheliogenesis.

Since a majority of human cancers are derived from gastrointestinal, urogenital, and pulmobronchial epithelia, in which X or multimeric X antigens are strongly expressed at embryonic to fetal age, an intense reexpression of these antigens in a large variety of human cancers suggests that these structures are essentially oncofetal antigens. Only those cancer cells derived from epithelial tissues that express a high level of these antigens during a certain stage of development showed a strong reactivity with FH3 and FH4 antibodies. Interestingly, differentiated papillary adenocarcinoma of stomach expresses the antigen defined by FH4, whereas undifferentiated adenocarcinoma does not express this antigen. Thus, reexpression of the structure defined by FH4 in tumors could be associated with retrogenesis of tumor cells to a certain stage of organogenesis rather than to a stage of the very early embryo. If retrogenesis of cells occurs to a very early, undifferentiated stage of embryonic tissue, tumor cells may not express the FH4 antigen.

Figure 18:
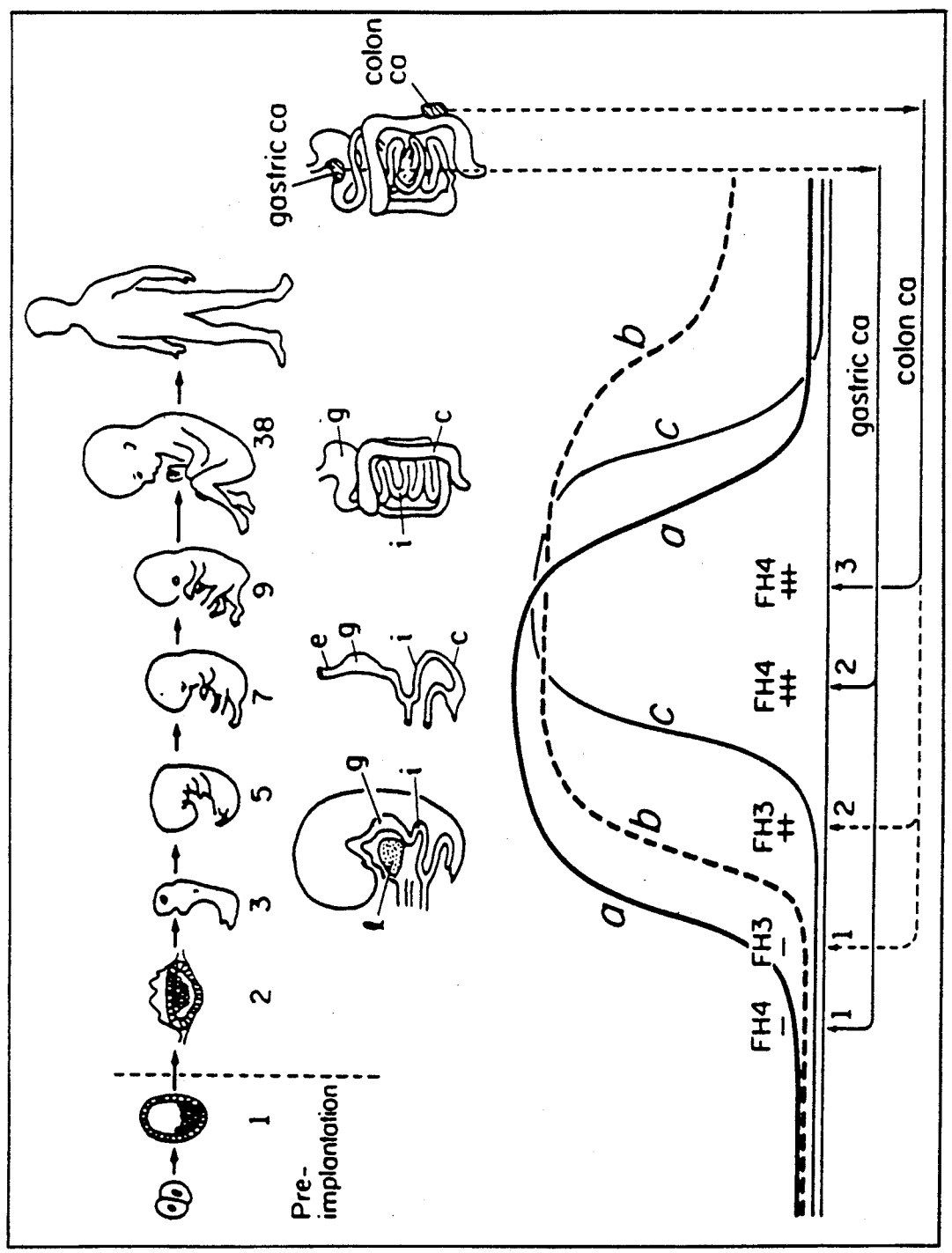
FIG. 18 is a diagrammatic representation of the stage-dependent expressions of X antigen (defined by FH3) and multimeric X antigen (defined by FH4) in gastrointestinal epithelia during human development as compared with the retrogenetic expression of the same antigens in gastrointestinal tumors, wherein the numbers at each stage of development represent weeks after fertilization, the ordinate indicates an arbitrary unit of antibody reactivity, the curves and arrows are coded as described in the specification, and the abbreviations are as follows: g for gastric epithelia, l for liver, i for intestine, and c for colon.

Referring to FIG. 18, the stage-dependent expressions of X antigen (defined by FH3) and di- or trimeric X antigen (defined by FH4) in gastrointestinal epithelia during human development, and the retrogenetic expression of these antigens in gastrointestinal tumors, are compared and contrasted. X and di- or trimeric X antigens may not be expressed in preimplantation embryo, although the X antigen is highly expressed in mouse preimplantation embryo. *Proc. Natl. Acad. Sci. U.S.A.* 75: 5565 (1978); *Biochem. Biophys. Res. Commun.* 100: 1578 (1981); *Nature (Lond.)* 292: 156 (1981). This possibility is suggested by the absence of the X antigen in undifferentiated human teratocarcinoma and the induction of antigen synthesis on differentiation, which is the opposite of mouse teratocarcinoma. The antigens, however, are expressed in various tissues of human postimplantation embryos and fetuses. Curves a and c illustrate the change in FH4 antigen expression in gastric and colonic epithelia, respectively. Curve b represents the change in FH3 antigen expression in colonic epithelia. FH4 expression in colonic epithelia reaches its maximum between 7 and 9 wk, then regresses almost completely, while the FH3 antigen does not regress and remains in the crypt cells. The FH4 antigen is strongly expressed in differentiated gastric cancer, suggesting that antigen retrogenesis occurs to the point at which FH4 expression is at its maximum (arrow 2). However, FH4 antigen expression is negative in undifferentiated gastric cancer because antigen retrogenesis occurs to a point at which FH4 is not yet expressed at the very early stages of embryogenesis (arrow 1). Both FH3 and FH4 antigen expression in colonic cancer could be strong if retrogenesis of the antigen expression occurs to the point at which the FH3 antigen is active.

Immunostaining of both X antigen and multimeric X antigen in paraffin-embedded sections gave similar or identical results to those from immunostaining of frozen cryostat sections. This may indicate that (a) glycolipid antigens are not diminished during preparation of paraffin sections, or (b) the antigens may be carried by glycoproteins that are not diminished by preparation of paraffin sections. Since many lacto-series carbohydrates are carried by both glycolipids and glycoproteins (*J. Biol. Chem.* 254: 5458, 1979), it is reasonable to assume that the antigens detected by immunostaining of fetal tissue sections are, in fact, glycoproteins with properties similar to "embryoglycan" or lactosaminoglycans (*Cell* 18:183, 1979).

Oncofetal expression of both FH3 and FH4 should be based on a common mechanism for activation of $\alpha 1 \rightarrow 3$ fucosyltransferase in fetal epithelial tissue and in certain types of human cancer. The fucosyltransferase that makes FH4 antigen can be distinguished from that for synthesis of FH3 antigen, and the genetic regulation of these enzymes is a crucial mechanism controlling embryogenesis and oncogenesis as well.

THIRD SERIES OF EXPERIMENTS

The antigens defined by monoclonal antibodies FH1, 2, 3, 4, 5, and ACFH18 were not detectable by regular radioimmunoassay methods in serum or plasma of patients with various cancers.

Tumor detection method using these antibodies

Because the antigens were not detectable by regular radioimmunoassay, the above-stated antibodies may not be immediately useful for diagnosis of human cancer by simple application of existing in vitro radioimmunoassay methodology. However, there is a strong possibility that the antigens are present in body fluids of cancer patients but at low concentration.

On the other hand, tumor antigens with great releasability are less useful for imaging than those antigens localized in tumor tissue. *New England J. Medicine* 298: 1384–1388 (1978). The antigens defined by FH3 and FH4 are highly restricted to differentiated human cancer, and their restricted presence in normal tissue is well defined. Thus it is contemplated that radiolabeled antibodies FH3 and FH4 will be particularly useful for imaging tumor location in vivo. For example, a radionuclide such as I-123 can be coupled to the antibody using standard methodologies, such as those employing the Bolton-Hunter reagent. The radiolabeled antibody can be admixed in a suitable carrier solution and intravenously injected into the body of a mammal. The body can be thereafter scanned with scintillation detector means, such as a gamma camera, to localize tumor tissue bearing antigens reactive with the radiolabeled antibody.

Immunotherapy of human cancer with these antibodies

The FH series and ACFH18 antibodies, particularly the IgG3 antibodies FH3 and FH4, are also suitable for cancer immunological therapy. Any of these antibodies can be coupled to a radionuclide or antitumor drug and intravenously injected into the body of a mammal to differentially deliver the radionuclide or drug to tissues bearing antigens reactive with the antibody. In view of the recent application of IgG3 antibody directed to a glycolipid antigen that suppresses tumor growth in vivo, (*Proc. Natl. Acad. Sci. USA* 82: 1242–1246, 1985), the IgG3 antibodies FH4 and FH3 are considered to be very good candidates for immunotherapy via direct intravenous injection of unconjugated antibody. Although the antigens reactive with FH4 and FH3 are present in kidney tubules, there is a possibility that the antigen may be cryptic in normal tissues, in view of recent reports as cited immediately above and also in *J. Immunol.* 132: 2111–2116 (1984).

While the present invention has been described in conjunction with preferred embodiments, one of oridinary skill after reading the foregoing specification will be able to effect various changes, substitutions of equivalents, and alterations to the compositions and methods set forth herein. It is therefore intended that the protection granted by Letters Patent hereon be limited only by the definitions contained in the appended claims and equivalents thereof.

The embodiments of the invention in which an exclusive property or privilege is claimed are defined as follows:

1. A radiolabeled antibody consisting of a monoclonal antibody specifically binding with a fucosylated type 2 chain structure selected from the group consisting of $III^3V^3Fuc_2nLc_6$ and $III^3V^3VII^3Fuc_3nLc_8$ but not specifically binding with any of $III^3FucnLc_4$, $V^3FucnLc_6$, $III^3FucnLc_6$, and $VI^2FucnLc_6$, coupled to a radionuclide.

2. The radiolabeled antibody of claim 1, wherein the monoclonal antibody is produced by hybridoma cell line ATCC No. HB8775.

3. A radiolabeled antibody consisting of a monoclonal antibody specifically binding with fucosylated type 2 chain structure $III^3V^3VII^3Fuc_3nLc_8$ but not specifically binding with any of $III^3FucnLc_4$, $III^3FucnLc_6$, and $VI^2FucnLc_6$, coupled to a radionuclide.

4. The radiolabeled antibody of claim 3, wherein the monoclonal antibody is produced by hybridoma cell line ATCC No. HB8770.

5. A method of immunohistological detection of cells bearing a glycolipid with di- or trifucosylated type 2 chain structure comprising the steps of contacting the cells with an immunological binding partner under conditions which allow binding between cells and the immunological binding partner to occur, and detecting immunological binding partner binding on the cells, wherein the immunological binding partner is an antibody or an antigen binding fragment thereof, that specifically bind with at least one fucosylated type 2 chain structure selected from the group consisting of difucosyl neolactonorhexaosylceramide ($III^3V^3Fuc_2nLc_6$) and trifucosyl neolactonorhexaosylceramide ($III^3V^3VII^3Fuc_3nLc_8$).

6. The method of claim 5, wherein the cells are cancer cells.

7. The method of claim 6, wherein the cells are selected from the group consisting of stomach, colon, and breast cancer cells.

* * * * *

UNITED STATES PATENT AND TRADEMARK OFFICE
CERTIFICATE OF CORRECTION

PATENT NO. : 5,171,667
DATED : December 15, 1992
INVENTOR(S) : S.-i. Hakomori et al.

Page 1 of 4

It is certified that error appears in the above-identified patent and that said Letters Patent is hereby corrected as shown below:

| COLUMN | LINE | |
|---|---|---|
| Title page, [54] and column 1 | 2 & 3 | "MONO-, DI-" should read --DI-- |
| 1 | 38 | "norhexaosylceramide" should read --norhexaosylceramide-- |
| 2 | 3 | "di-or" should read --di- or-- |
| 2 | 13 | "produced" should read --(produced-- |
| 2 | 14 | after "cell" insert --line ATCC No. HB8770)-- |
| 2 | 14 | after "ACFH18" delete "line ATCC No. HB8770" and insert --,-- |
| 3 | 66 | "neolactonorhexaosylceramide" should read --neolactonoroctaosylceramide-- |
| 13 | 7 | "paraffinembedded" should read --paraffin-embedded-- |
| 17 (Table IV) | 29 | "Other cells   -, +" should read --Other cells   -, +‡-- |
| 17 (Table IV) | 45 | " -, Three of four cases;" should read --‡-, Three of four cases;-- |
| 20 | 27 | "espphageal" should read --esophageal-- |
| 20 | 57 | after "Biol." insert --18:-- |
| 22 | 55 & 56 | "oridi-nary" should read --ordinary-- |
| [56] "Other Publications" | 1st Publ. | "d-" should read --di-- |

UNITED STATES PATENT AND TRADEMARK OFFICE
CERTIFICATE OF CORRECTION

PATENT NO. : 5,171,667
DATED : December 15, 1992
INVENTOR(S) : S.-i. Hakomori et al.

It is certified that error appears in the above-identified patent and that said Letters Patent is hereby corrected as shown below:

| COLUMN | LINE | |
|---|---|---|
| [56] "Other Publications" | 2nd Publ. | "gly-cosphinolipids" should read --glycosphingolipids-- |
| [56] "Other Publications" | 10th Publication | Please add --Fukushi, Y., et al., Novel fucolipids accumulating in human adenocarcinoma. III. A hybridoma antibody (FH6)$_3$ defining a human cancer-associated difucoganglioside (VI$^3$NeuAcV$^3$III$^3$Fuc$_2$nLc$_6$), *J. Biol. Chem.* 259(16):10511-10517, 25 August 1984. |
| [56] "Other Publications" | 11th Publication | Fukushi, Y., et al., Localization and alteration of mono-, di-, and trifucosyl $\alpha 1 \rightarrow 3$ type 2 chain structures during human embryogenesis and in human cancer, *J. Exp. Med.* 159:506-520, August 1984. |
| [56] "Other Publications" | 12th Publication | Hakomori, S.-i., et al., Novel fucolipids accumulating in human adenocarcinoma. I. Glycolipids with di- or trifucosylated type 2 chain, *J. Biol. Chem.* 259(7):4672-4680, 10 April 1984. |
| [56] "Other Publications" | 13th Publication | Hakomori, S.-i., et al., Human cancer-associated gangliosides defined by a monoclonal antibody (IB9) directed to sialosyl$\alpha$ $2 \rightarrow 6$ galactosyl residue: a preliminary note, *Biochem. Biophys. Res. Comm.* 113(3):791-798, 1983. |

UNITED STATES PATENT AND TRADEMARK OFFICE
CERTIFICATE OF CORRECTION

PATENT NO. : 5,171,667

DATED : December 15, 1992

INVENTOR(S) : S.-i. Hakomori et al.

It is certified that error appears in the above-identified patent and that said Letters Patent is hereby corrected as shown below:

| COLUMN | LINE | |
|---|---|---|
| [56] "Other Publications" | 14th Publication | Hakomori, S.-i., et al., The common structure in fucosyllactosamino-lipids accumulating in human adenocarcinomas, and its possible absence in normal tissue, *Biochem. Biophys. Res. Comm.* 109(1):36-44, 1982. |
| [56] "Other Publications" | 15th Publication | Hakomori, S.-i., et al., The hapten structure of a developmentally regulated glycolipid antigen (SSEA-1) isolated from human erythrocytes and adenocarcinoma: a preliminary note, *Biochem. Biophys. Res. Comm.* 100(4):1578-1586, 1981. |
| [56] "Other Publications" | 16th Publication | Young W. W., et al., Production of monoclonal antibodies specific for two distinct steric portions of the glycolipid ganglio-N-triosylceramide (asialo $GM_2$), *J. Exp. Med.* 150:1008-1019, 1979. |
| [56] "Other Publications" | 17th Publication | Yang, H-j., and S.-i Hakomori, A sphingolipid having a novel type of ceramide and lacto-N-fucopentaose III, *J. Biol. Chem.* 246(5):1192-1200, 1971. |

UNITED STATES PATENT AND TRADEMARK OFFICE
CERTIFICATE OF CORRECTION

PATENT NO. : 5,171,667
DATED : December 15, 1992
INVENTOR(S) : S.-i. Hakomori et al.

It is certified that error appears in the above-identified patent and that said Letters Patent is hereby corrected as shown below:

| COLUMN | LINE | |
|---|---|---|
| [56] "Other Publications" | 18th Publication | Abe, K., et al., The monoclonal antibody directed to difucosylated type 2 chain (Fuc$\alpha$1$\rightarrow$2Gal$\beta$1$\rightarrow$4[Fuc$\alpha$1$\rightarrow$3]GlcNAc; Y determinant), *J. Biol. Chem.* 258(19):11793-11797, 1983.-- |

Signed and Sealed this

Second Day of November, 1993

Attest:

BRUCE LEHMAN

*Attesting Officer*   *Commissioner of Patents and Trademarks*